(12) United States Patent
Osorio

(10) Patent No.: US 9,095,303 B2
(45) Date of Patent: Aug. 4, 2015

(54) SYSTEM AND APPARATUS FOR EARLY DETECTION, PREVENTION, CONTAINMENT OR ABATEMENT OF SPREAD ABNORMAL BRAIN ACTIVITY

(75) Inventor: Ivan Osorio, Leawood, KS (US)

(73) Assignee: FLINT HILLS SCIENTIFIC, LLC, Lawrence, KS (US)

(*) Notice: Subject to any disclaimer, the term of this patent is extended or adjusted under 35 U.S.C. 154(b) by 495 days.

(21) Appl. No.: 13/449,166

(22) Filed: Apr. 17, 2012

(65) Prior Publication Data

US 2012/0265262 A1 Oct. 18, 2012

Related U.S. Application Data

(63) Continuation-in-part of application No. 13/308,913, filed on Dec. 1, 2011, now Pat. No. 8,989,863, which is a continuation-in-part of application No. 13/280,178, filed on Oct. 24, 2011, which is a (Continued)

(51) Int. Cl.
*A61N 1/00* (2006.01)
*A61B 5/00* (2006.01)
(Continued)

(52) U.S. Cl.
CPC ............ *A61B 5/4094* (2013.01); *A61B 5/0476* (2013.01); *A61B 5/4848* (2013.01); *A61N 1/36064* (2013.01); *A61N 1/36114* (2013.01); *A61N 1/36139* (2013.01); *A61N 1/36146* (2013.01); *A61B 5/021* (2013.01);
(Continued)

(58) Field of Classification Search
CPC ........... A61N 1/36064; A61N 1/36067; A61N 1/36135

USPC ................................................. 607/45, 9, 2
See application file for complete search history.

(56) References Cited

U.S. PATENT DOCUMENTS 5,938,689 A 8/1999 Fischell et al.
6,597,954 B1 7/2003 Pless et al.
(Continued)

FOREIGN PATENT DOCUMENTS

EP 1609414 A2 12/2005
WO 20060050481 A1 5/2006

OTHER PUBLICATIONS

International Application No. PCT/US2013/036885, International Search Report and Written Opinion dated Jul. 26, 2013, 12 pages.
(Continued)

*Primary Examiner* — Christopher D Koharski
*Assistant Examiner* — Philip Edwards

(57) ABSTRACT

A method, comprising detecting an epileptic event in a neural network, wherein the event occurs in a first node; identifying a second node; and applying a therapy to the second node or any connection. A method, comprising determining a first body index indicative of epileptic activity; monitoring a second body index; detecting an indication of activity spread, based upon at least the second body index; and taking a responsive action, such as delivering therapy, modifying therapy, logging the indication, or warning. A method, comprising detecting an epileptic event in a first node of a neural network; applying a first therapy to a first neural structure for treating the event; and applying a second therapy to a second neural structure of the patient based on an event spread proclivity to a third neural structure. A non-transitive, computer-readable storage device for storing data that when executed by a processor, perform a method.

9 Claims, 21 Drawing Sheets

Related U.S. Application Data continuation-in-part of application No. 12/729,093, filed on Mar. 22, 2010, now Pat. No. 8,560,073.

(60) Provisional application No. 61/210,850, filed on Mar. 23, 2009.

(51) Int. Cl.
| | |
|---|---|
| *A61B 5/0476* | (2006.01) |
| *A61N 1/36* | (2006.01) |
| *A61N 1/05* | (2006.01) |
| *A61N 1/362* | (2006.01) |
| *A61B 5/021* | (2006.01) |
| *A61B 5/024* | (2006.01) |
| *A61B 5/0402* | (2006.01) |
| *A61B 5/11* | (2006.01) |
| *A61B 5/16* | (2006.01) |
| *A61B 5/18* | (2006.01) |

(52) U.S. Cl.
CPC ............ *A61B 5/024* (2013.01); *A61B 5/02405* (2013.01); *A61B 5/0402* (2013.01); *A61B 5/11* (2013.01); *A61B 5/16* (2013.01); *A61B 5/18* (2013.01); *A61B 5/7264* (2013.01); *A61N 1/0529* (2013.01); *A61N 1/3621* (2013.01)

(56) References Cited

U.S. PATENT DOCUMENTS

| | | | |
|---|---|---|---|
| 7,006,859 | B1 | 2/2006 | Osorio et al. |
| 7,551,956 | B2 | 6/2009 | Osorio et al. |
| 8,337,404 | B2 | 12/2012 | Osorio |
| 8,382,667 | B2 | 2/2013 | Osorio |
| 2002/0072782 | A1* | 6/2002 | Osorio et al. ................ 607/45 |
| 2007/0250134 | A1* | 10/2007 | Miesel et al. ................ 607/45 |
| 2008/0077191 | A1 | 3/2008 | Morrell |
| 2011/0160795 | A1 | 6/2011 | Osorio |
| 2011/0251468 | A1 | 10/2011 | Osorio |
| 2011/0270096 | A1 | 11/2011 | Osorio et al. |
| 2012/0046711 | A1 | 2/2012 | Osorio |
| 2012/0078323 | A1 | 3/2012 | Osorio |
| 2012/0226108 | A1 | 9/2012 | Osorio |
| 2012/0271372 | A1 | 10/2012 | Osorio |

OTHER PUBLICATIONS

Barkley GL, Smith B, Bergey G, Worrell G, Drazkowski J, Labar D, Duchrow R, Murro A, Smith M, Gwinn R, Fish B, Hirsch L, Morrell M (2006). Safety and preliminary efficacy of a responsive neurostimulator. Neurology (Suppl 2);A387.
Boeijinga PH, Lopes da Silva F. A new method to estimate time delays between EEG signals applied to beta activity of the olfactory cortical areas. Electroencephal Clin Neurophysiol 1989; 73:198-205.
Boyden ES, Zhang F, Bamberg E, Nagel G, Deisseroth K. Millisecond-timescale, genetically targeted optical control of neural activity. Nat Neurosci. 2005;8:1263-8.
Dudek FE, Obenaus A, Tasker JG. Osmolality-induced changes in extracellular volume alter epileptiform bursts independent of chemical synapses in the rat: importance of non-synaptic mechanisms in hippocampal epileptogenesis. Neurosci Lett 1990;120-267-70.
Dutertre F. Origin and transformation of the electrical activities which result in the electroencephalogram. In Remond A. (Chief Ed.) Handbook of Electroencephalography and Clinical Neurophysiology vol. 11, Part A Semiology in Clinical EEG 1977 pp. 11A-5-15.
Popovych, et al.; "Synchronization Control of Interacting Oscillatory Ensembles by Mixed Nonlinear Delayed Feedback;" Phys Rev. E 82, 026204; 2010; 7 pgs.
Fisher RS, SANTE Study Group (2006). Stimulation of the Anterior Nucleus of the Thalamus for Epilepsy. Interim Report Epilepsia 47: 332.
Fox JE, Bikson M, Jefferys JGR. Tissue resistance changes and the profile of synchronized neuronal activity during ictal events in the low calcium model of epilepsy. J Neurophysiol 2004; 92:181-88.
Freeman, JZ, et al.; "A Technique for Current Density Analysis of Field Potentials and its Applicaion to the Frog Cerebellum;" Institute of Biomedical Research; Freeman and Stone; pp. 421-427.
Gopalsami et al, "SAW Microsensor Brain Implant for Prediction and Monitoring of Seizures;" IEEE Sensors Journal, vol. 7, No. 7, Jul. 2007; pp. 977-982.
Kazhdan et al, "Shape Matching and Anisotropy;" SIGGRPAH; 2004; pp. 623-629.
Koreniewska, et al, "Determination of Information flow Direction Among Brain Structures by a Modified Direct Transfer Functions (dDTF) Method;" Journal of Neuroscience Methods; May 2003; pp. 195-207.
Krim, et al, "Two Decades of Array Signal Processing Research. The Paramedic Approach;" IEEE Signal Processing Magazine; vol. 13, Issue 4; Jul. 1996; pp. 67-94.
Kaminski et al, "Determination of EEG Activity Propagation: Pairwise Versus Multichannel Estimate;" IEEE Transactions on Bio-Medical Electronics; vol. 51, Issue 9; Sep. 2004; pp. 1501-1510.
Lai et al., "Characterization of Synchrony with Applications to Epileptic Brain Signals;" Physical Review Letters; PRL 98, 108102 (2007); pp. 1-4.
DaSilva et al., "Interdependence of EEG Signals: Linear vs. Nonlinear Associations and the Significance of Time Delays and Phase Shifts;" Brain Topography, vol. 2, Nos. 1/2, 1989; pp. 9-18.
Mackey et al., "Dynamical Diseases;" Annals of the New York Academy of Sciences; vol. 504; 1987; pp. 16-32.
Mendel, J.M.; "Tutorial on Higher-Order Statistics (Spectra) in Signal Processing and System Theory; Theoretical Results and Some Applications;" Proceedings of the IEEE, vol. 79, No. 3; Mar. 1991; pp. 278-305.
Osorio et al., "Automated Seizure Abatement in Humans Using Electrical Stimulation;" Annals of Neurology; vol. 57, Issue 2; Feb. 2005; pp. 258-268.
Osorio, et al., "Seizure Abatement with Single DC Pulses: Is Phase Resetting at Play?" International Journal of Neural Systems, vol. 19, No. 3 (2009); pp. 149-156.
Osorio, et al., "Neuronal Synchronization and the "Ictio-centric" vs the Network Theory for Ictiogenesis: Mechanistic and Therapeutic Implications for Clinical Epileptology;" Seizure Prediction in Epilepsy; 2008; pp. 109-115.
Osorio, et al., "Pharmaco-Resistant Seizures: Self-Triggering Capacity, Scale-Free Properties and Predictability;" vol. 30; Issue 8; Oct. 2009; pp. 1554-1558.
Osorio, et al., "Probabilistic Definition of Seizures;" 2010; pp. 1-23.
Osorio, et al.; "Real-Time Detection, Quantification, Warning, and Control of Epileptic Seizures: The foundations for a Scientific Epileptology;" Epilepsy & Behavior, vol. 16, Issue 3; 2009; pp. 391-396.
Osorio, et al; "Seizure Control with Thermal Energy? Modeling of Heat Diffusivity in Brain Tissue and Computer-based design of a Prototype Mini-Cooler;" Epilepsy & Behavior, vol. 16, Issue 2; 2009; pp. 203-211.
Osorio, et al; "Towards an Objective, Quantitative Characterization and Definition of Epileptic Seizures;" pp. 1-25.
Phillips; "Unit Activity Recording in Freely Moving Animals; Some Principles and Theory;" Brain Unit Activity During Behavior; 1973; pp. 5-40.
Kaminski; et al; "Determination of EEG Activity Propagation: Pair-Wise Versus Multichannel Estimate;" IEEE Transactions on Bio-Medical Electronics; vol. 51, Issue 9; 2004; pp. 1501-1510.
Sunderam et al.; "The Study of Temporal Distribution of Seizure Occurrences;" Temporal Interdependency of Seizures; pp. 78-84.
Tasaki; "New Measurement of Action Currents Developed for Single Nodes of Ranvier;" Journal of Neurophysiology; vol. 27; 1964; pp. 1199-1206.
Popovych et al.; "Control of Neural Synchrony by Nonlinear Delayed Feedback;" Biol Cybern (2006) 95: 69-85.
Popovych et al.; "Effective Desynchronization by Nonlinear Delayed Feedback;" Phys. Rev. Lett. 94 (2005) 164102; 4 pgs.

\* cited by examiner

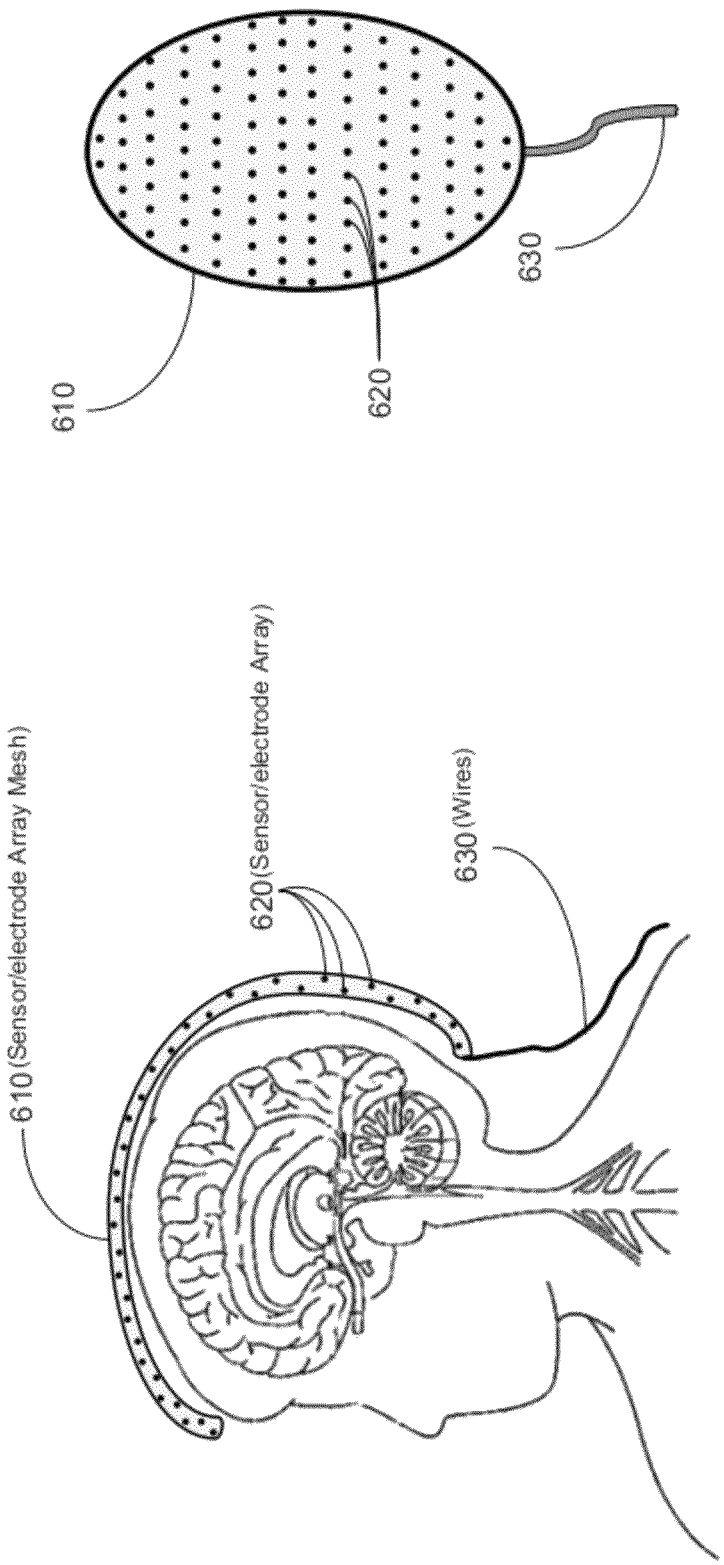

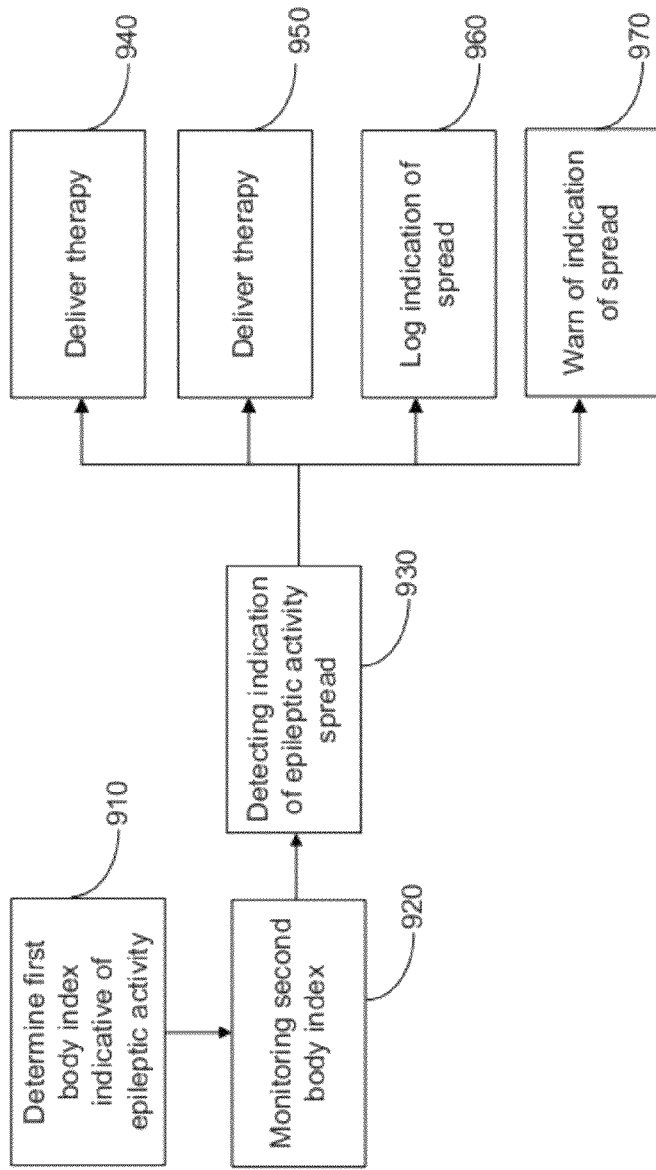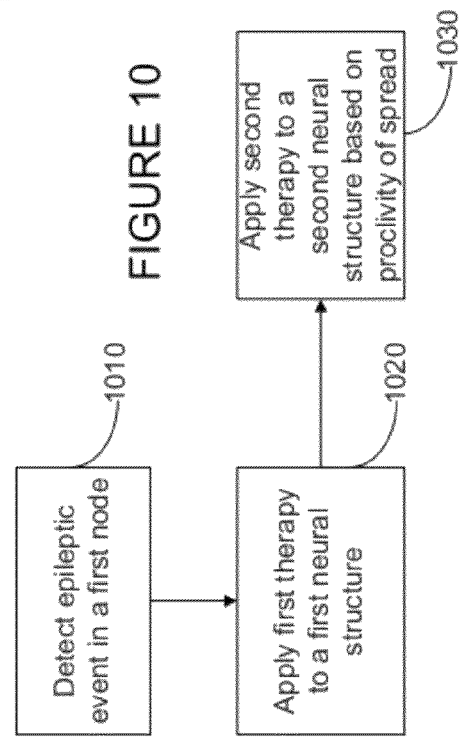

SYSTEM AND APPARATUS FOR EARLY DETECTION, PREVENTION, CONTAINMENT OR ABATEMENT OF SPREAD ABNORMAL BRAIN ACTIVITY

CROSS-REFERENCE TO RELATED APPLICATIONS

This application is a continuation-in-part of U.S. patent application Ser. No. 12/729,093, entitled "System and Apparatus for Automated Quantitative Assessment, Optimization and Logging of the Effects of a Therapy," filed Mar. 22, 2010 and currently pending, which claimed priority from co-pending U.S. provisional patent application No. 61/210,850, entitled "System and Apparatus for Automated Quantitative Assessment, Optimization and Logging of the Effects of a Therapy," filed Mar. 23, 2009. This application is also a continuation-in-part of U.S. patent application Ser. No. 13/280,178, entitled "Method, System, and Apparatus for Automated Termination of a Therapy for an Epileptic Event Upon a Determination of Effects of a Therapy," filed Oct. 24, 2011, currently pending, and is also a continuation-in-part of U.S. patent application Ser. No. 13/308,913, entitled "System and Apparatus For Increasing Regularity and/or Phase-Locking of Neuronal Activity Relating to an Epileptic Event," filed Dec. 1, 2011, currently pending. U.S. Ser. No. 13/308,913 is a continuation-in-part of U.S. Ser. No. 13/280,178, which is a continuation-in-part of U.S. Ser. No. 12/729,093. All applications referred to above are hereby incorporated by reference in their entirety.

Safe and effective therapies for pharmaco-resistant seizures are a major unmet medical need affecting approximately 36% of all epileptics (~1.1 million in the US and ~18 million worldwide). These subjects have poor quality of life, the large majority are unemployed, suffer from depression and are 40 times more likely to die suddenly than age-matched subjects in the general population. Brain electrical stimulation, either directly or indirectly (vagus nerve stimulation), and contingent (e.g., triggered by the onset of seizures) or non-contingent (e.g., periodic, round-the-clock), and other therapies such as localized cooling of the epileptogenic zone or direct delivery of drugs to it, hold great promise for these patients. However, in light of the results of large recent clinical trials showing a modest mean decrease in seizure frequency of 40-60% on patients than remain on multiple anti-seizure drugs, optimization is required if they are meet efficaciously and cost-effectively this medical need. This disclosure addresses in a novel, effective, and systematic manner, the complex and demanding task of optimization of interventional brain therapies for control of undesirable changes of state. In its preferred embodiment this disclosure addresses brain state changes and in particular epileptic seizures. Therapies for other neurological (e.g., pain, movement), psychiatric (e.g., mood; obsessive compulsive), and cardiac (e.g., arrhythmias) disorders may be optimized using the approaches described herein.

Epileptic seizures occur with or without discernible or visible clinical manifestations.

In the case of seizures originating from discrete brain regions (known as partial or "focal" seizures) the electrical abnormalities usually precede the first clinical manifestation (subjective or objective) and in a large number of these patients, impairment or loss of responsiveness occurs some time after the first clinical manifestation. Also, if the seizure becomes secondarily generalized, loss of consciousness (to be distinguished from loss of responsiveness) occurs after loss of responsiveness. Commonly, abnormal electrical activity outlasts the loss of consciousness and consciousness is regained before responsiveness returns to normal (for the patient) levels. In certain epileptic brains the transition from the non-seizure to the seizure state may be gradual, providing a window for prediction and intervention before the transition is complete. Degree of responsiveness may be tested and quantified in real-time using a wide variety of available tests.

Therapy for control of disorders such as epilepsy which manifest intermittently, aperiodically and briefly (ranging from seconds to rarely >2 min) and are classified as dynamic, meaning that state changes (from normal to abnormal and vice-versa) are caused by changes in the system's control parameter(s) are specially challenging. To increase the probability of therapeutic success local, global, structural, dynamical, and state factors influencing the state change, must be identified and measured with useful precision and at informative time scales. These concepts and considerations required to formulate treatment and optimization strategies are lacking in the state-of-the art therapies.

While this disclosure is aimed at optimizing a therapy for prevention of seizure spread or of emergence of seizure activity, nothing in its specification precludes delivery of a therapy prior to optimization or without optimization. Indeed, optimization cannot take place if a therapy has not been administered and its effects (beneficial or detrimental) quantified. If a therapy cannot be optimized (in terms of increasing its beneficial effects), optimization may be effected by decreasing the number, intensity, or duration of the therapy's adverse events. Adverse effects include but are not limited to increase in seizure frequency or severity, cognitive impairment in functions such as memory, language, or changes in mood (depression or mania), or in thought (psychosis). These adverse effects may be quantified using cognitive, electrical, thermal, optical and other signals and logged to computer memory. In the case of signals that lack easily detectable or recognizable electrical or other correlates, they may be characterized using a semi-quantitative approach such as psychiatric scales, care-giver observations or patient diaries.

The term "therapy" may be interchangeably used with the term control for which a theory exists (Control Theory) in the field of engineering. Since therapy and control share the same aim, it is appropriate to adopt certain concepts form this theory as well as from the fields of dynamics to generate a rational approach and strategy for the management of pharmaco-resistant seizures.

The epileptic brain may be conceptualized as a non-stationary, non-linear, "noisy" system that undergoes sudden unexplained reversible transitions from the non-seizure state. The manner in which this transition occurs may be "gradual" (through a process of "attractor deformation") or sudden (through a "leap" from one state to another) as observed in bi-stable or multi-stable systems. Dynamical theory teaches that a system may be defined by its dimension (which corresponds to the minimum number of variables required to specify it). The identification of a system's dimension greatly benefits from the identification of a spatio-temporal scale of observation that corresponds to a representative sample of the system (so-called mesoscopic scale), thus obviating the need to study the whole system at all scales, a daunting and impracticable task in the case of the mammalian brain. The epileptic brain's dimensionality and its mesoscopic scale have not been effectively specified to date. This knowledge void forces the treatment of the brain as a "black-box".

While by definition a "black-box" is not amenable to direct inquiry, it can be indirectly studied through perturbations of system inputs. A known, well characterized input is "fed" into the "black-box" and the output is carefully recorded and characterized quantitatively or qualitatively and compared to the input. Transformations, if any to the input properties provide indirect but useful information about the "black-box" that may be captured mathematically as transfer functions. For example, if doubling the amplitude of the input translates into doubling of the output, the system is considered linear. However if doubling the input causes an exponential increase in the output, the system is non-linear (likely the brain's case). If sine waves are fed into the black box and 60 Hz activity appears on them as they exit the box, it is reasonable to infer that the box corrupts the waves and is "noisy". Successful control of the behavior of "black-boxes" cannot occur if the measurements of its output are not representative of the state (s) and site(s) from where they are obtained, reasonably precise and also reproducible from measurement to measurement.

SUMMARY OF THE DISCLOSURE

The present disclosure provides a method, comprising detecting an epileptic event in a neural network within a brain of a patient, wherein said epileptic event in a first node of said neural network; identifying a second node of said neural network based at least in part on at least one coupling characteristic between said first node and said second node; and applying a therapy to said second node or any connection to said second node of said neural network, in response to said detecting.

The present disclosure also provides a method, comprising determining a first body index indicative of an epileptic activity in a patient; monitoring a second body index different from the first body index, in response to said determining; detecting an indication of epileptic activity spread in a brain of the patient, based upon at least said second body index; and taking a responsive action in response to said detecting, wherein said responsive action is selected from delivering a therapy to at least one neural structure of said patient, modifying a therapy to at least one neural structure of said patient, logging said indication of spread, or warning said patient, a caregiver, or a medical professional of said indication of spread.

The present disclosure also provides a method, comprising detecting an epileptic event in a first node of a neural network in the brain of a patient; applying a first therapy to a first neural structure of said patient for treating said epileptic event; and applying a second therapy to a second neural structure of said patient based on a proclivity of a spread of said epileptic event to a third neural structure of said patient.

The present disclosure also provides a non-transitive, computer-readable storage device for storing data that when executed by a processor, perform a method disclosed herein.

BRIEF DESCRIPTION OF THE DRAWING FIGURES

FIG. 1 depicts a medical device system, comprising an extra-cranial, cranial, or intra-cranial electrode implanted in a patient, in accordance with one illustrative embodiment of the present disclosure.

FIG. 2 presents a block diagram of a medical device system, in accordance with one illustrative embodiment of the present disclosure.

FIG. 3 presents a block diagram of a medical device system, in accordance with one illustrative embodiment of the present disclosure.

FIGS. 6A and 6B show a stylized depiction of a sensor/electrode array mesh, in accordance with one illustrative embodiment of the present disclosure.

Figure 7A:
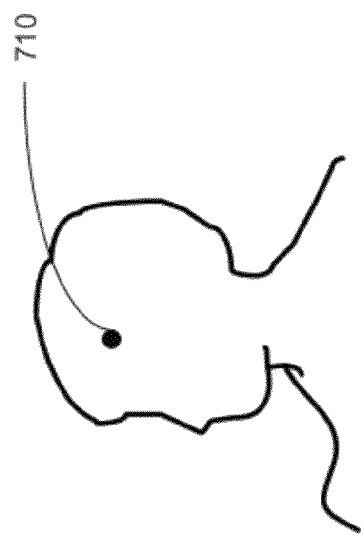
FIG. 7A illustrates a stylized depiction of a site of emergence of abnormal electrical activity in a patient's brain, in accordance with one illustrative embodiment of the present disclosure.
Figure 7B:
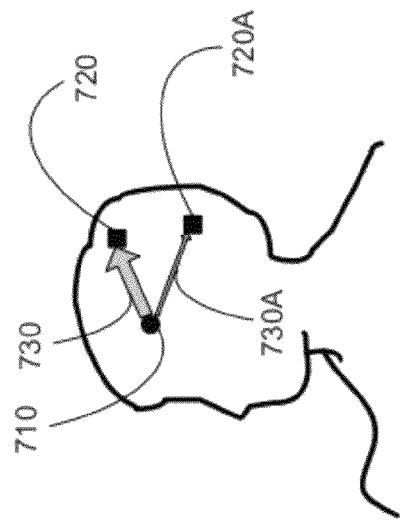
FIG. 7B illustrates a stylized depiction of a stored reference spread mapping of abnormal electrical activity, in accordance with one illustrative embodiment of the present disclosure.
Figure 7C:
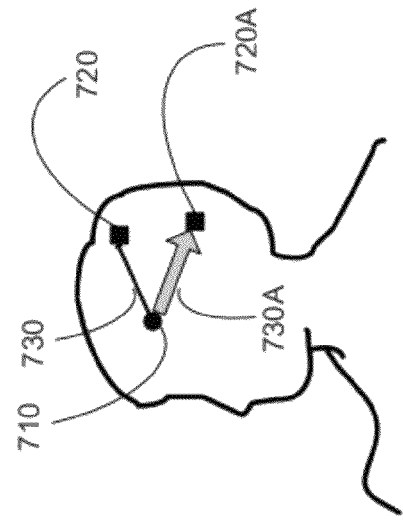
Figure 7D:
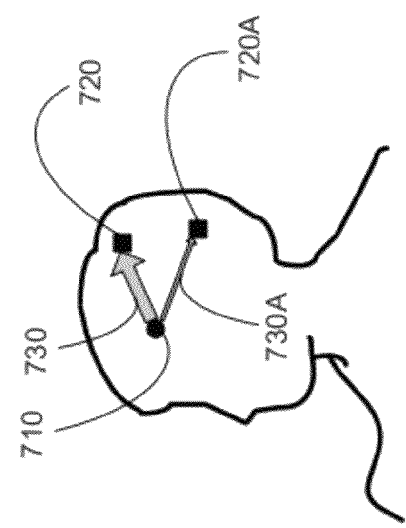

FIGS. 7C and 7D illustrate a stylized depiction of a real-time detection of abnormal electrical activity, determination of the likelihood of spread to different node or hub within the same network or to a different network based among others on estimation of a gradient, identification of the most likely spread target(s) and a comparison to a reference spread mapping, in accordance with one illustrative embodiment of the present disclosure.

Figure 8:
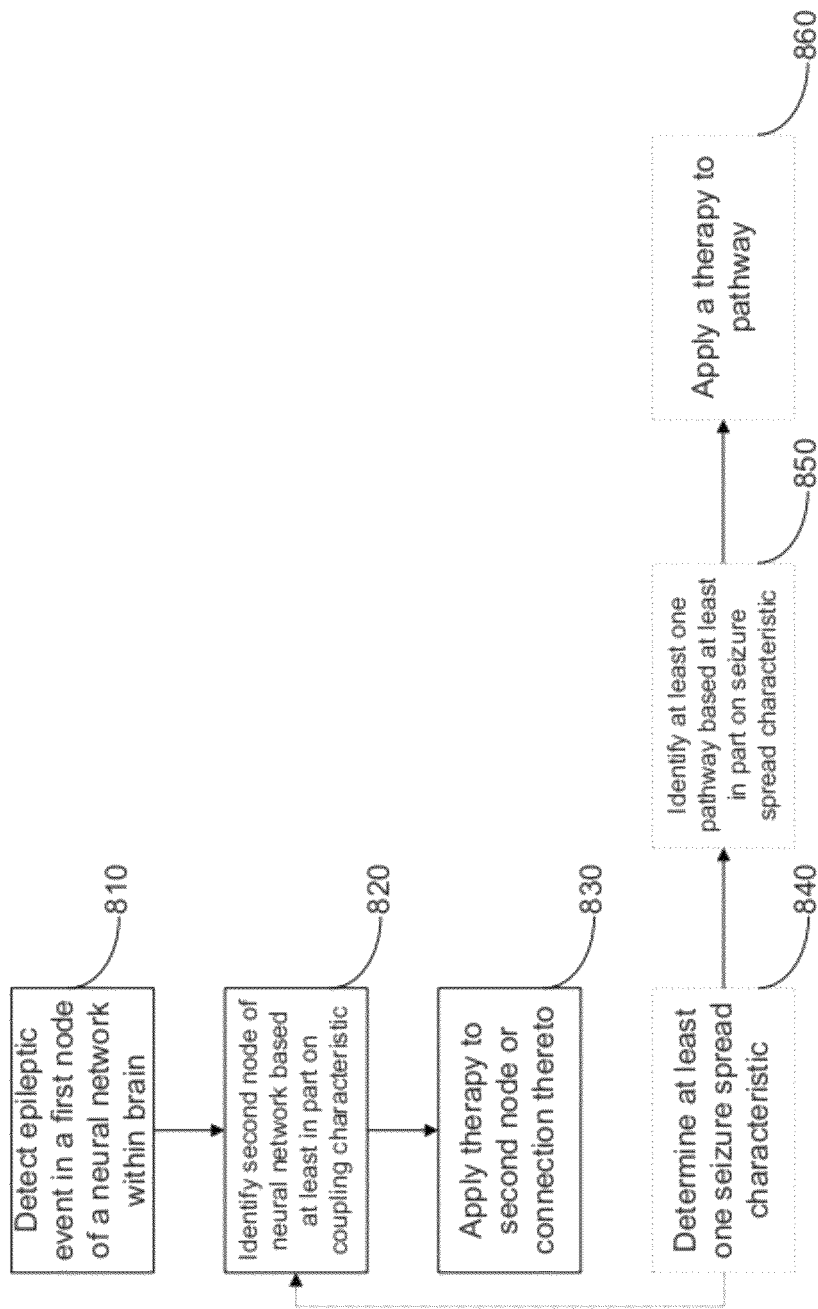

FIG. 8 shows a flowchart depiction of a method, in accordance with one illustrative embodiment of the present disclosure.

FIG. 9 shows a flowchart depiction of a method, in accordance with one illustrative embodiment of the present disclosure.

FIG. 10 shows a flowchart depiction of a method, in accordance with one illustrative embodiment of the present disclosure.

Figure 11:
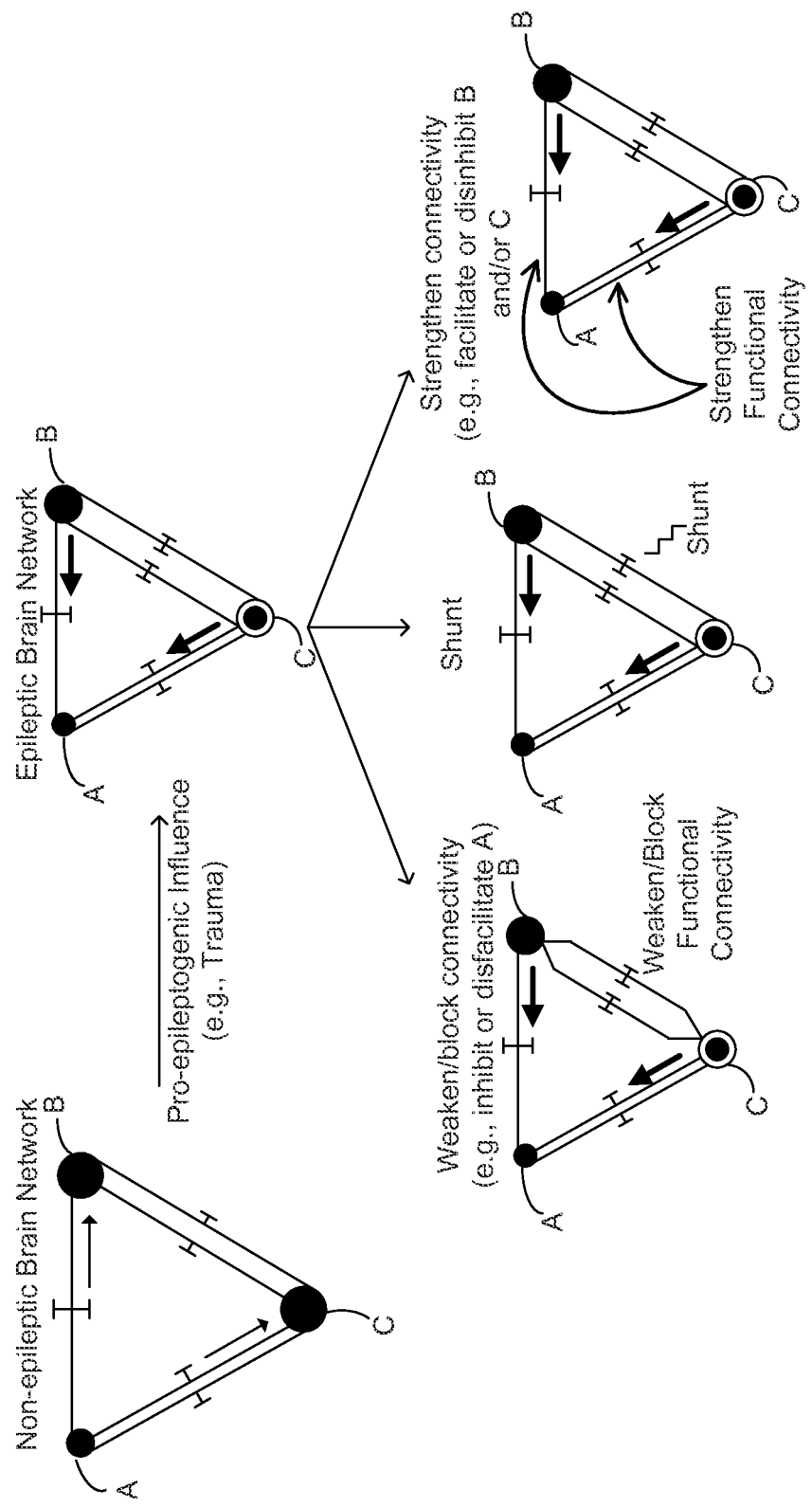

FIG. 11 shows an exemplary depiction of how epileptic event spread may be blocked, in accordance with one illustrative embodiment of the present disclosure.

Figure 12:
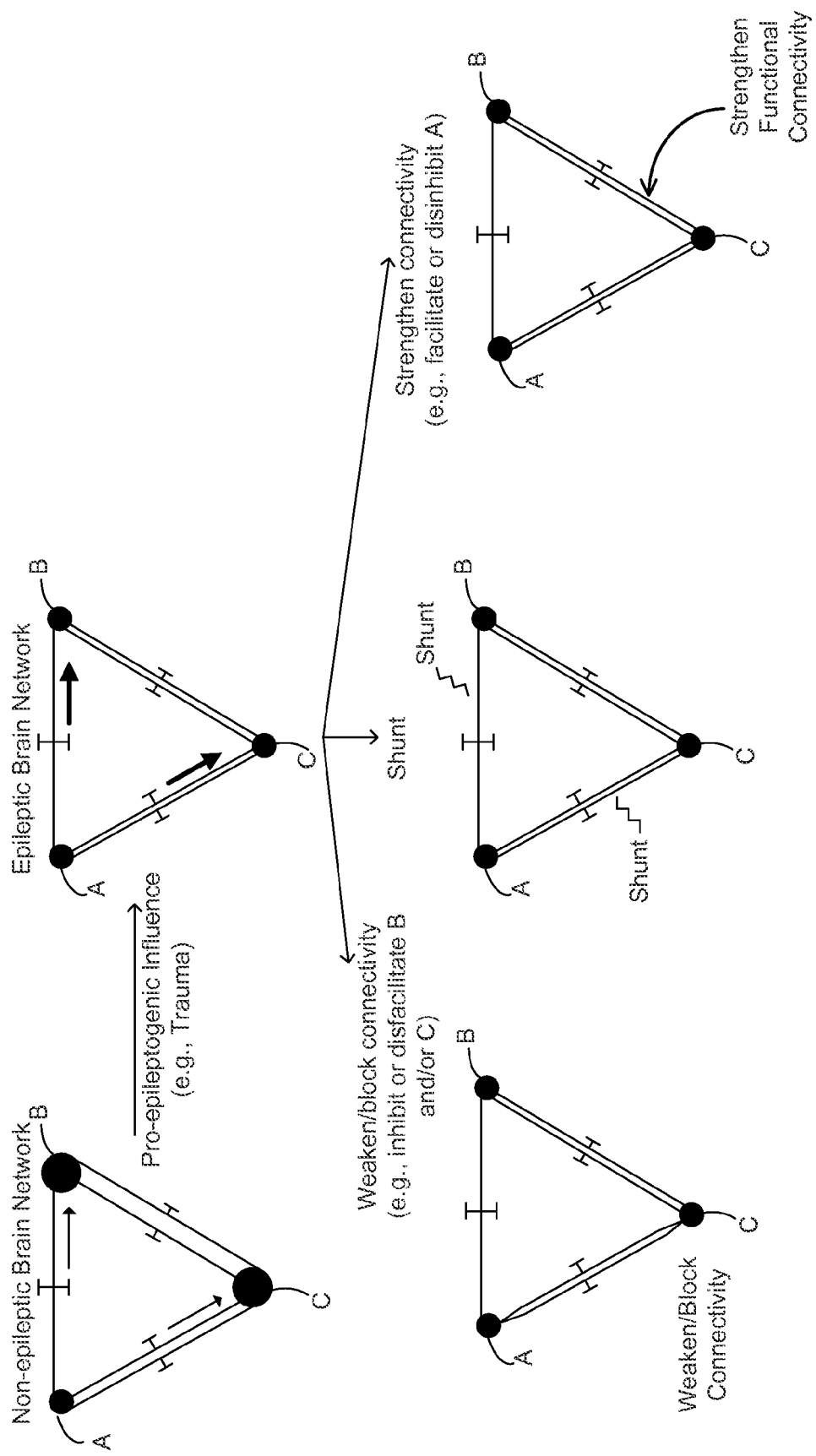

FIG. 12 shows an exemplary depiction of how epileptic event spread may be blocked, in accordance with one illustrative embodiment of the present disclosure.

FIG. 13 shows changes in functional connectivity under three different task conditions (13A, 13B, and 13C) among various frontal or temporal lobe brain regions, in accordance with one illustrative embodiment of the present disclosure.

Figure 14:
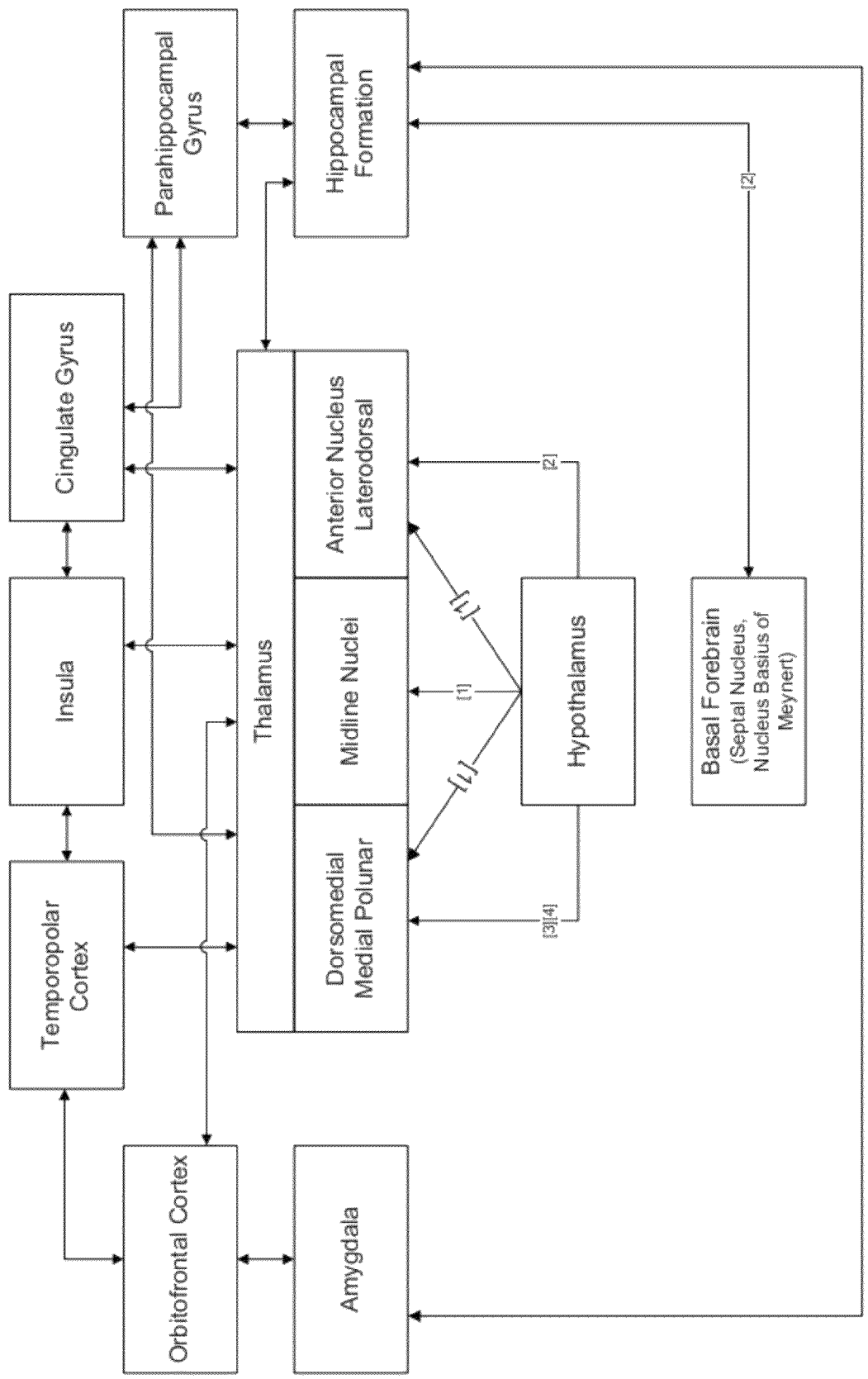

FIG. 14 shows structural connectivity among various brain regions, in accordance with one illustrative embodiment of the present disclosure.

Figure 15:
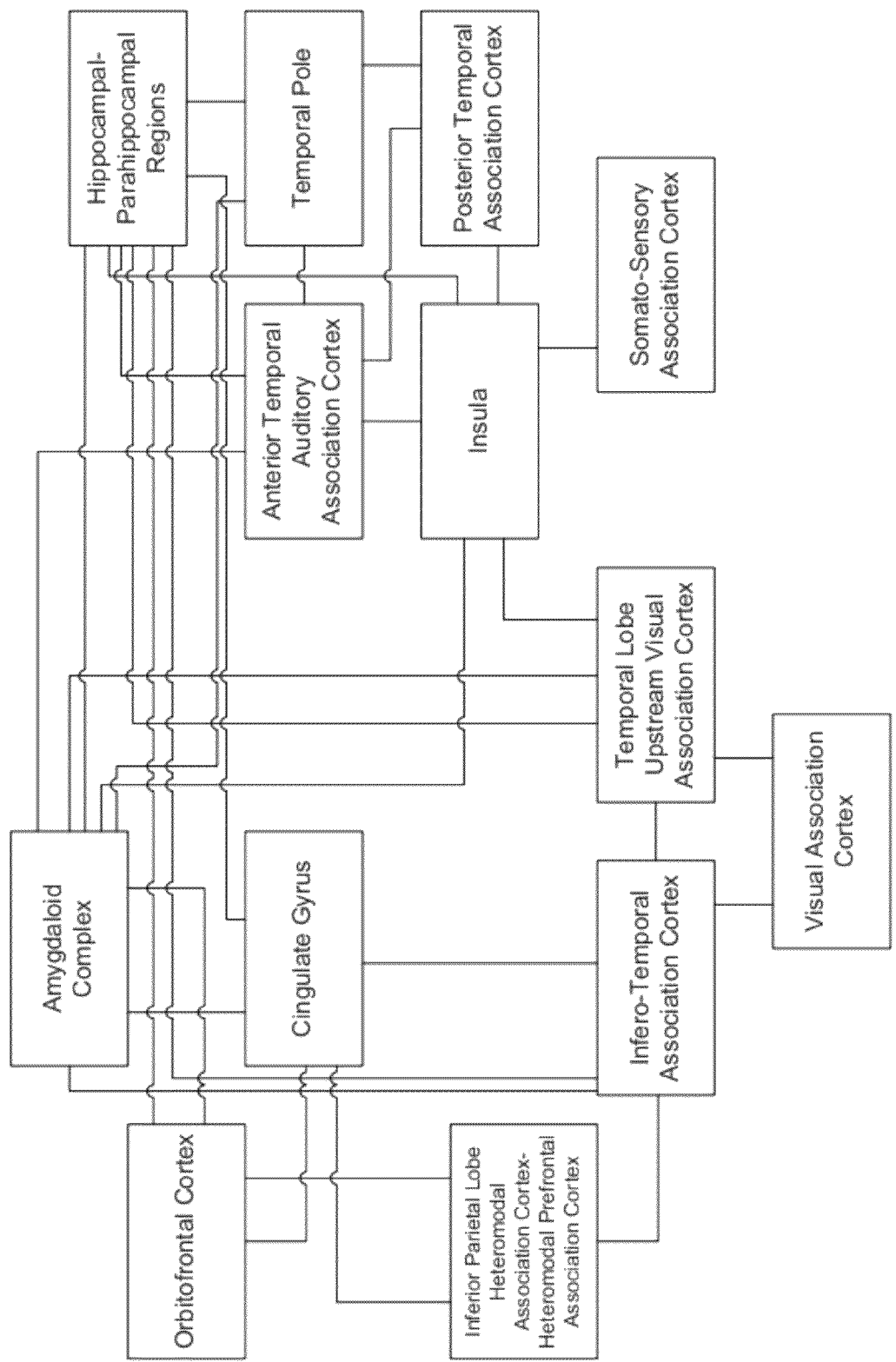

FIG. 15 shows structural connectivity among various brain regions, in accordance with one illustrative embodiment of the present disclosure.

Figure 16:
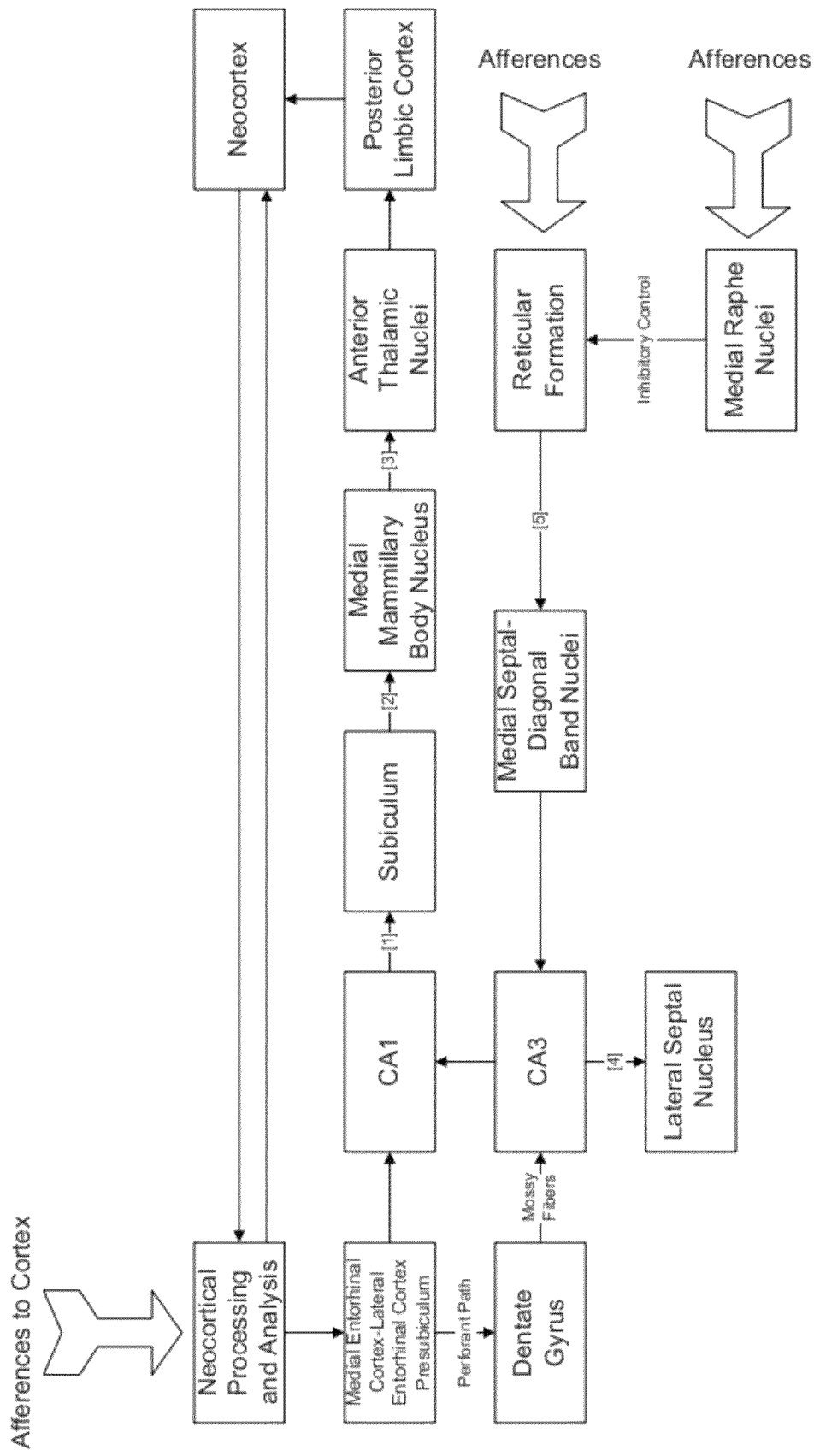

FIG. 16 shows structural connectivity among various brain regions, in accordance with one illustrative embodiment of the present disclosure.

Figure 17:
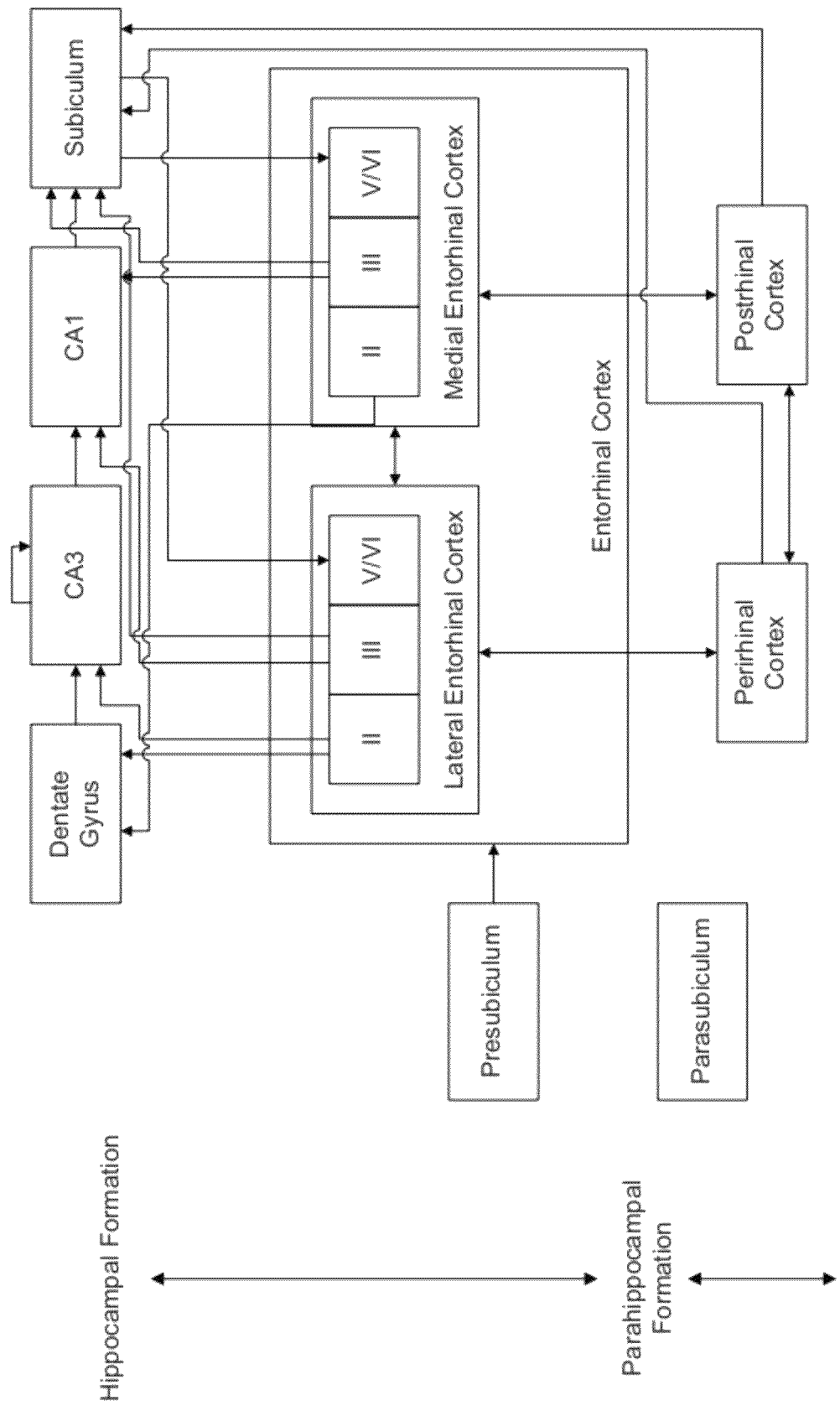

FIG. 17 shows structural connectivity among various brain regions, in accordance with one illustrative embodiment of the present disclosure.

Figure 18:
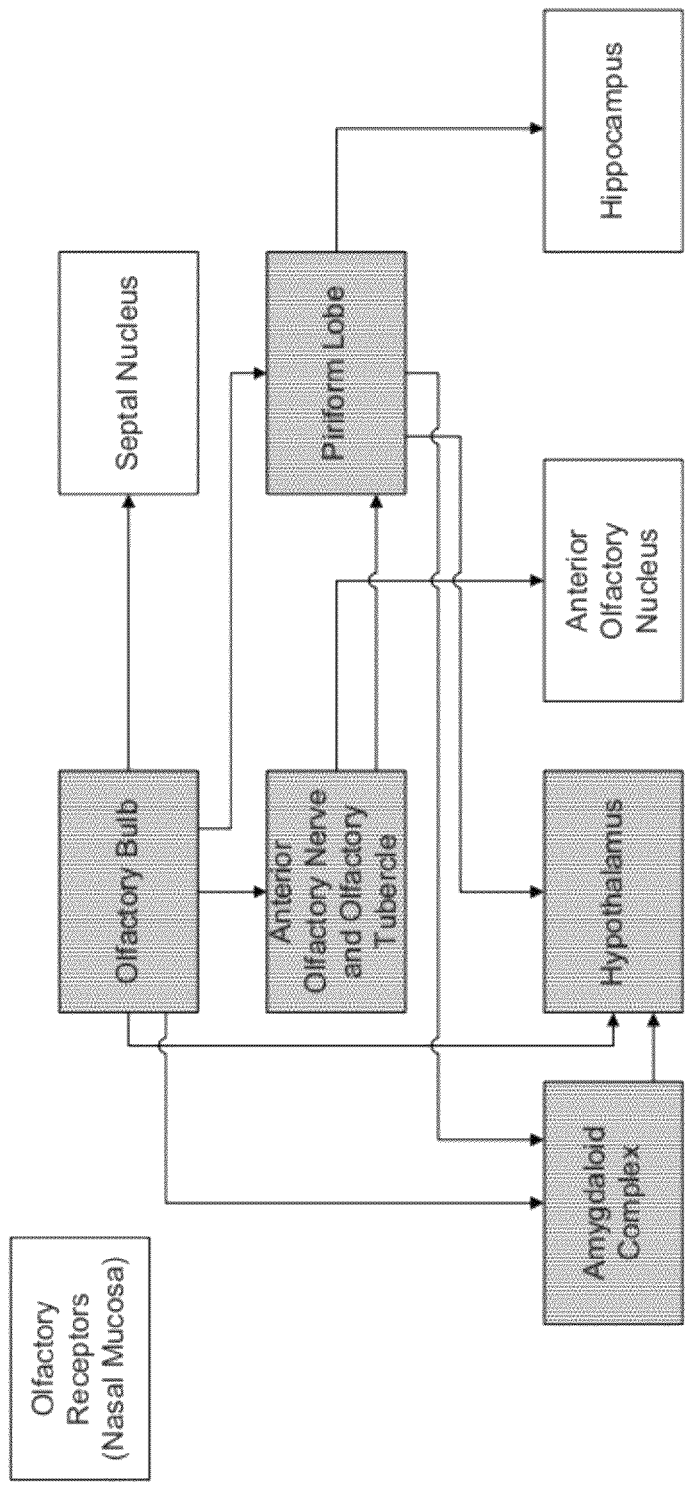

FIG. 18 shows structural connectivity among various brain regions forming one neural network (all depicted structures) comprising a subnetwork (stippled depicted structures), in accordance with one illustrative embodiment of the present disclosure.

Figures 19, 20:
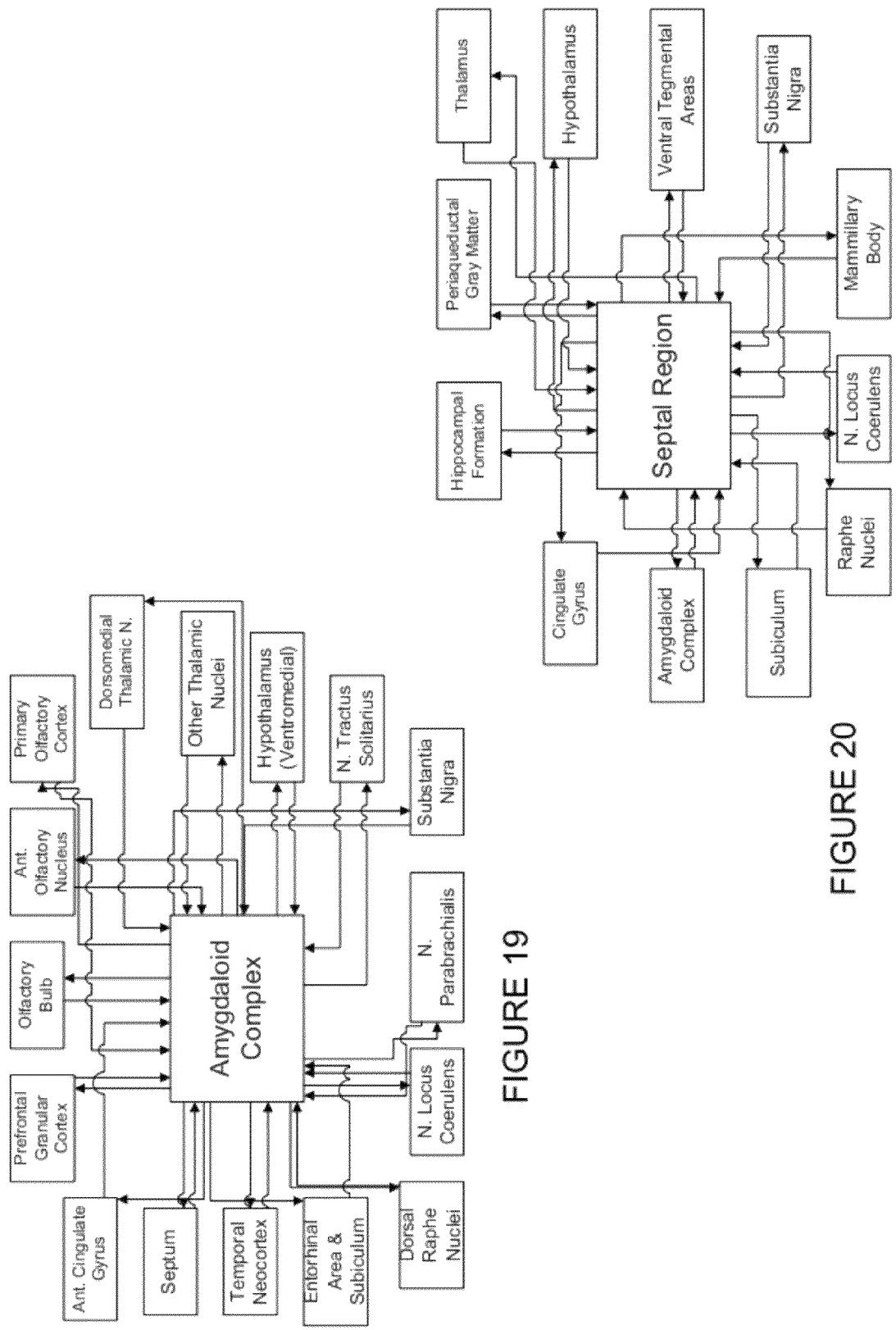

FIG. 19 shows structural connectivity among various brain regions, in accordance with one illustrative embodiment of the present disclosure.

FIG. 20 shows structural connectivity among various brain regions, in accordance with one illustrative embodiment of the present disclosure.

Figure 21:
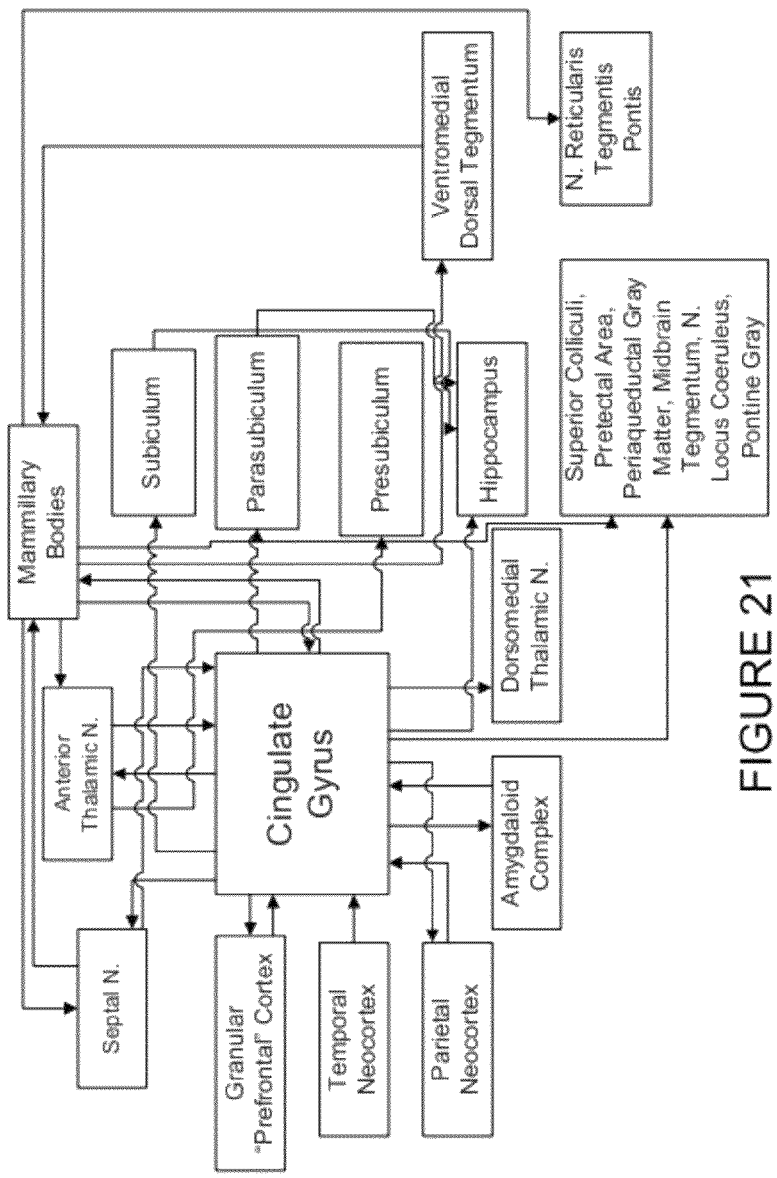

FIG. 21 shows structural connectivity among various brain regions, in accordance with one illustrative embodiment of the present disclosure.

Figure 22:
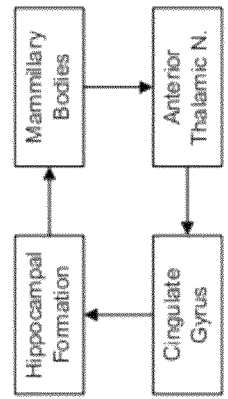

FIG. 22 shows structural connectivity among various brain regions, in accordance with one illustrative embodiment of the present disclosure.

Figure 23:
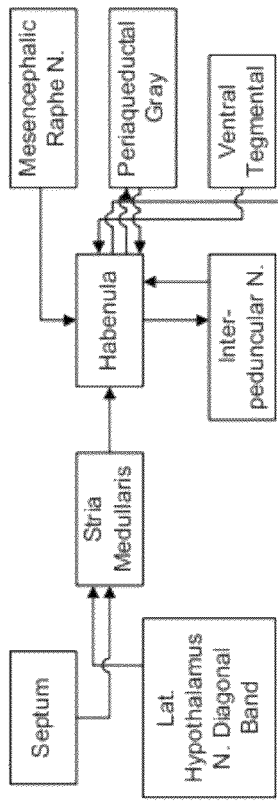

FIG. 23 shows structural connectivity among various brain regions, in accordance with one illustrative embodiment of the present disclosure.

Figure 24:
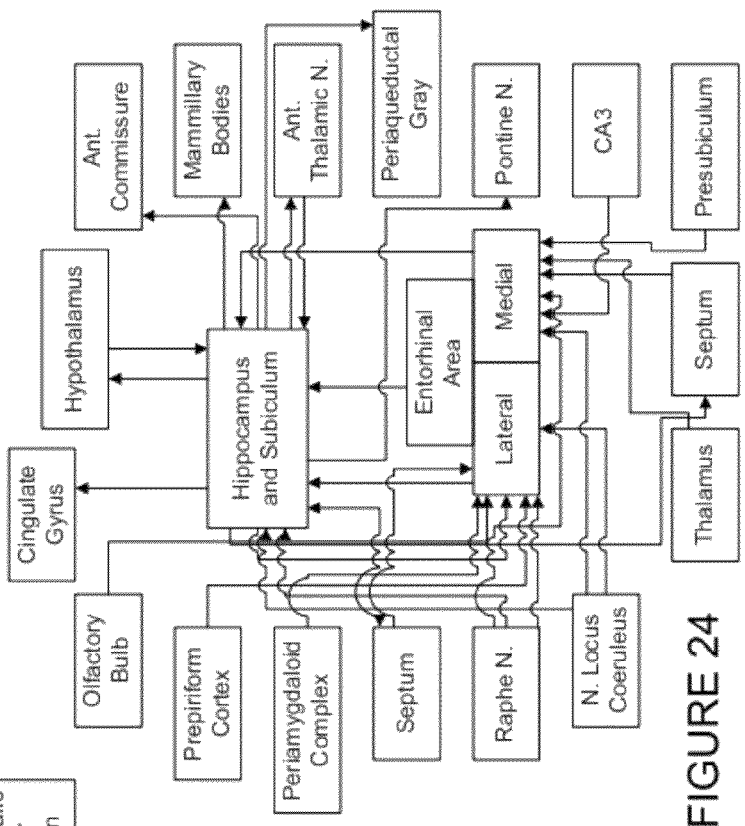

FIG. 24 shows structural connectivity among various brain regions, in accordance with one illustrative embodiment of the present disclosure.

Figure 25:
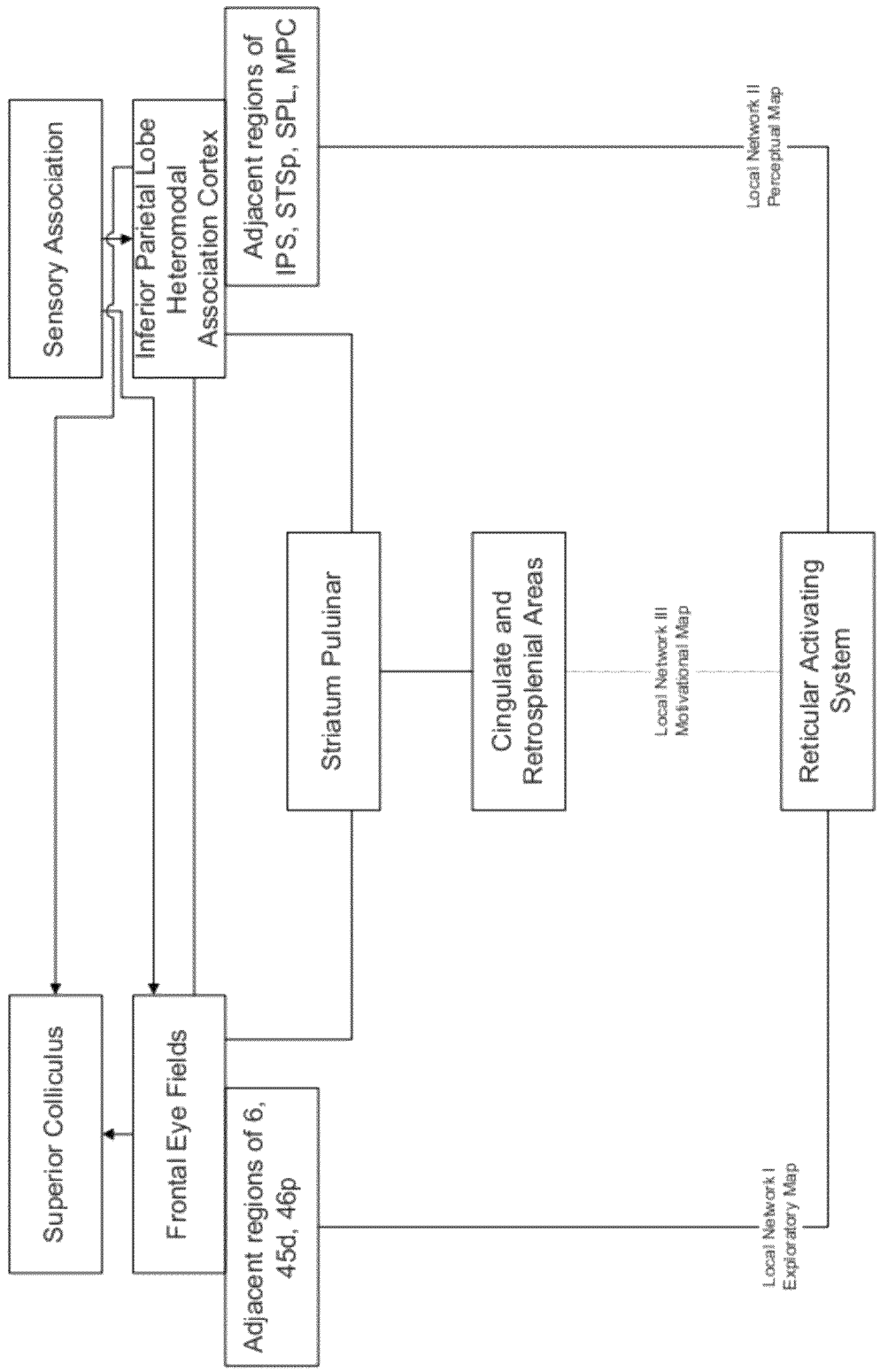

FIG. 25 shows structural connectivity among various brain regions, in accordance with one illustrative embodiment of the present disclosure.

DETAILED DESCRIPTION OF THE DISCLOSURE

Historically, in epileptology, the study of seizure generation (referred herein to as ictogenesis) has been anatomically and functionally restricted to the so-called "focus" or epileptogenic zone, defined as the location in the brain where seizures originate. This concept connotes that ictogenesis depends only on mechanisms inherent to the neuronal assembly(es) that make up the "focus", which in this model are largely if not entirely autonomous from and not susceptible to larger scale (intra- or inter-regional) interactions. The "seizure focus" theory (which may be referred to herein as the "ictio-centric" or "ictiocentric" theory) ignores the anatomo-functional connectivity, albeit probably aberrant, between the site where a seizure first emerges and regions connected to the "emergence site" that partake in its elicitation, progression and cessation as demonstrated in animals and also probably in humans. In short, the "focus" concept, which this disclosure overcomes or surmounts, disregards the brain as being an assembly of networks organized on at least three spatial scales: (i) individual neurons and synapses (microscale); (ii) neuronal groups and populations (e.g., macro-columns) (mesoscale); and (iii) anatomically distinct cyto-architectonic areas and their corresponding inter-areal pathways (macroscale). The term "focus" is used herein solely to refer to the "focus theory" which this disclosure does not espouse.

Seizure blockage triggered by automated detections is the state of the art in clinical epileptology. While based on a sound rationale, this line of attack is valuable only if a seizure is suppressed before it reaches a critical mass and spreads by continuity/contiguity to neighboring tissue, or via pathways/connections to distant structures. For the probability of the spread to remain low once a seizure occurs: a) therapy delivery must take place shortly (e.g. not to exceed 5 seconds) after detection of a manifestation; b) the therapy onset of action must be immediate, and (c) its therapeutic ratio must be high. Since the "penalty" to the patient would be unacceptably high (unawareness or loss of consciousness and risk of injuries in the case of complex partial or generalized seizures) if blockage fails, a safer, clinically more valuable and efficient strategy is early, rapid detection and automated containment of the seizure, to prevent the initial epileptogenic mass from growing to a critical size, so as to minimize the probability of spread outside a primary epileptogenic network. This strategy is also more efficient than the one currently practiced as the energy/dose required to prevent spread to uninvolved tissue is lower than that needed to revert a state change and likely more efficacious since the tissue treated has not been seized by pathological activity. Once spread is prevented, or simultaneously with the intervention required to accomplish this objective, the seizure may be also blocked.

This disclosure provides a method and a system/apparatus for early, rapid seizure detection, prevention of spread, blockage if indicated (e.g., the seizure starts in a critical (for adaptive behavior) node or hub) and also modeling/prediction of their mode and preferred route of spread and its targets. Moreover, in one embodiment, if at onset, a seizure has low probability of spread and/or if its severity is low and/or the site of emergence is not critical for preservation of highly valued functions such as wakefulness with awareness, postural tone, or cardio-respiratory integrity, it may be more efficient, safer, and more tolerable (as no adverse affects would occur) to withhold treatment. This approach may also be more physiological than indiscriminate treatment, since being "relaxation phenomena", seizure blockage or suppression may lead to further accumulation of energy that may result, as observed in a clinical trial, in an increase in the severity of subsequent seizures, a shortening of the time to the next seizure or both.

The human brain may be regarded as a "super-" or "mega-network" composed of a large number of networks spanning several scales from microscopic (e.g. neuronal mini-column), through mesoscopic (e.g. hippocampal formation), to macroscopic (e.g. limbic system) to megascopic (e.g., the brain). Accurate and worthwhile characterization a network's behavior may be achieved with a branch of mathematics called graph theory. Graph theory furnishes insight into the structure/topology, distribution degree, clustering, and path length, among other properties, that allow for characterization and modeling of: a) Normal and abnormal network behavior; b) Transitions between states and how to prevent them or spatio-temporally contain them. Graph theory also provides information about the vulnerability of a network to "attack", in this case by a seizure or other pathological activity, the negative impact of said "attack" on its function and means to manage it.

Terms such as "node", "hub", "edge" which are common usage in graph theory, will be applied in this disclosure to certain central nervous system neuronal-astrocytic ensembles and pathways. Quantifiable properties such as clustering coefficient, path, length or centrality, will be determined to characterize the topology and behavior of a network as a function of time/state and other variables. It is remarked that a subset of a network, or more than one network may be studied simultaneously and also that depending on its scale/size and state, a network component may correspond to a "hub" in one embodiment and to a "node" in a different embodiment.

The central nervous system and particularly, cortical and sub-cortical neuronal/astrocytic ensembles, correspond dynamically to "oscillators" with state-dependent (variable) coupling strength. The behavior of variably coupled oscillators may be determined through measurements of frequency, amplitude and phase, from which coherence, synchronization or information (e.g., entropy) measurements may be derived. State of the art epileptology extracts these observables at inadequate spatio-temporal scales (it surveys only the site of seizure "origin") and this through a narrow portal as allowed by the "focus" (ictio-centric) theory. This unduly reductionist theory: 1. Disregards the flow of "information" between an epileptogenic network and other networks to which is connected and thus their potential role in the triggering, progression and termination of seizures; 2. It conceptualizes abnormal neurological manifestations of a seizure, stroke or other disorders as solely the product of a local lesion or dysfunction, ignoring among others, the contribution of fibers or projections from other regions, that course through the damaged tissue (See Catanio and Mesulam's article in Cortex 2008; 44:953-961 for a detailed exposition of the pitfalls of this traditional conceptualization). Functional magnetic resonance imaging (f MRI) studies of patient with stroke, reveal for example, that abnormal interactions among undamaged cortical regions remote from the ischemic lesion, contribute to the motor deficit; modulation of these undamaged regions with transcranial magnetic stimulation causes improvement in function.

A model in which the responsivity ("hodological resonance") of a network to incoming information becomes abnormally high so that a seizure is triggered and which is adopted in one embodiment in this disclosure, finds no support or place in the "focus" theory.

While in epileptology there is a recent impetus to study synchronization in order to gain insight into the dynamics of the generation and spread of seizures, its scope is limited to the presumed epileptogenic zone discounting the role of regions connected to it and other factors such as state of the network(s), its/their topology (e.g., small world vs. power law distributed), rate and direction of information flow and level of coupling among oscillators, without which proper and clinically useful characterization of their behavior/dynamics cannot be realized. Directed transfer functions are used in this disclosure to explore functional connectivity within a network or between networks. The variant reconnectivity construction is achieved with the Kalman filter algorithm which can incorporate time varying state equations. Those skilled in the art acknowledge that this information may also be extracted from the minimum spanning tree of global correlations.

The mutation of a network from non-epileptogenic into epileptogenic, may be dependent on the network size and architecture. Epileptogenic networks may be characterized by a low cluster coefficient and high path length. Using fMRI, or diffusion tensor imaging, along with tractography the degree of epileptogenicity of a network may be determined and using exogenous or endogenous intervention these two properties (cluster coefficient and/or path length among others) may be modified to prevent spread, control the seizure and even possibly transform the network into non-epileptogenic. For example, in one embodiment, reversible inhibition or destruction (lesioning) of a connector hub in a network may be therapeutic as it increases the small world index, and with it the flow and rate of information within a network or between networks. In another embodiment, reversible or irreversible blockage, deceleration or perturbation of impulse/information conduction along edges (pathways) connecting nodes, hubs or nodes and hubs (an action that modifies anatomical or functional/effective path length) using electrical, chemical, thermal, mechanical or endosomatic means, may be to prevent seizure emergence or spread.

In yet another embodiment, concepts of parallel distributed processing are applied to prevent seizure spread and whenever needed to abate the seizure using physical (e.g. electrical, thermal, mechanical) chemical (e.g., drugs, amino acids, ions) mechanical (e.g., negative or positive pressure) or endosomatic (e.g. "biofeedback", cognitive or sensory activation) means.

Unlike artificial or other non-biological neural networks, the properties of those putative to the brain, especially the brain of man, have: a) much higher dimensionality and complexity emerging from, among other factors, redundancy/overlap of connections, recurrent axonal collaterals (fibers that originate from and terminate in the same neuron), and the existence of fibers "en passage" (fibers originating in a structure passing through another without forming synapses with it on their way to yet another structure where synaptic connections do occur); b) plasticity/remodeling capabilities structurally and functionally/dynamically; c) functional state-dependency; d) emergent properties, which resist proper and thorough characterization by reductionist approaches.

The present disclosure conceptualizes seizures as emergent network behavior that is causally irreducible to a singular part (e.g., the "focus") of a network. It further acknowledges that while brain states such as seizures may arise out of a multiplicity of relatively simple interactions, what "emerges" (e.g., a seizure) cannot be reduced to the system's disassembled/isolated constituent parts. More specifically, this disclosure takes into account that even in-depth, thorough, and accurate characterization of the behavior of each and every component of an epileptogenic network in isolation from the others, will not inform on the mechanisms of ictiogenesis and thus furnish little, if any, insight into how to predict seizures, prevent them from occurring, or prevent them from spreading within or between networks if prevention fails. Inherent to this substantive departure from the conventional, commonly-accepted "focus" theory, is neural intervention (e.g., modulation) at an appropriate network spatio-temporal scale (e.g., micro-, meso-, or macroscopic) according to the sensitivity, precision, and accuracy of the prediction/detection system; the network(s) scale, topology and dynamics; the latency of onset of action; efficacy; and adverse effects of the therapy in use.

For example, if monitoring neuronal mini-columns in a network allows timely, consistent detection of time of seizure emergence, but the therapy's onset of action is so slow that delivery to the site of emergence would not be efficacious, blockage of spread becomes the main viable alternative. In this case, treatment at the meso-scale level may be indicated, resulting in a "trans-scale" approach (e.g., prediction or detection at the microscopic and delivery of therapy at the mesoscopic level).

The present disclosure also adopts a "complex systems theory" approach (e.g., the whole is greater than the sum of its parts) as befits the high complexity-dimensionality of the human brain and its ability to readily interact with the environment (inner and outer). These characteristics are borne, from among others, out of the: a) redundancy/overlap of connections, recurrent axonal collaterals and of fibers en passage (fibers originating in a structure passing through another (without forming synapses with it) on their way to another structure where synaptic connections do occur); b) plasticity/remodeling capabilities structurally and functionally/dynamically; c) functional state-dependency and optimized network topology (e.g., small world).

A clinical case studied by this inventor illustrates seizures as an emergent network property. A patient with pharmaco-resistant seizures was evaluated for surgery with bi-temporal depth electrodes and subdural strips placed over both orbitofrontal regions. Seizures emerged independently in this case from both mesial temporal regions and while those on left outnumbered those on the right, resective surgery was not performed since it would not have been curative. This patient agreed to participate in a clinical trial (approved by the inventor's institution's human subjects committee) to demonstrate feasibility and safety of high frequency electrical stimulation triggered by automated detections of seizure onset. The left mesial temporal region was chosen as the stimulation target since the majority of seizures emerged from this region. High frequency stimulation abated seizures emerging from this site, likely prevented seizure occurrence on the right mesial temporal region but led to the emergence of seizures on the left orbito-frontal region which, while not part of the limbic network, is connected to it. In other words, suppression of seizures on the left mesial frontal may have disinhibited (or excited) the ipsilateral orbito-frontal region leading to seizure emergence in this region.

Another example of seizures as a network property, and more specifically, of the efficacy of therapeutic intervention outside the epileptogenic network (a trans-network effect), is found in the audiogenic seizure rodent model. The epileptogenic network in this rat model is constituted by the inferior (IC) and superior (SC) colliculi, pontine reticular formation (PRF), and periaqueductal gray (PAG). Seizures may be blocked with drugs that suppress neuronal activity in the IC or other sites of the network. Remarkably, the NMDA receptor channel blocker, MK-801, blocks audiogenic seizures even though it does not depress neuronal firing in any of this network's constituents. MK-801 likely suppresses seizures through excitation of neurons in the substantia nigra reticulata, but only in the intact animal and not in vitro. That this compound not only acts on the non-epileptogenic network, but notably has no effect on the disassembled network (IC, SC and PRF) brings to the fore the relevance and clinical utility of the network theory concepts adopted in this disclosure. The focus theory would not predict the observed trans-network effect, and would have erroneously predicted an in vitro ("focal") effect, which was not observed.

The "trans-network" phenomenon is likely not limited to beneficial therapeutic effects as observed in rats with audiogenic epilepsy. This "trans-network" phenomenon, which may be an example of "hodological resonance", may be also used in one embodiment in this disclosure for early seizure detection, that is, before a first manifestation occurs in the network of emergence (customary network). By tracking the certain cerebral or extra-cerebral signal properties or certain information measures, the occurrence of a seizure may be signaled before the appearance (in the customary network) of the universally accepted hallmark of seizure onset: ictal electrical activity. The signal properties or certain information measures may include, but are not limited to, (i) power at certain frequencies, wave morphology, etc., (ii) degree of synchronization, (iii) spatial extent of synchronization, and/or (iv) an entropy, and the analyses may be performed: (a) within the customary network, (b) between it and other network(s), and/or (c) within or between networks connected to the customary network (but excluding the customary network).

Since there is no universally accepted single notion of what is an "emergent" property or behavior, this disclosure incorporates all notions such as that which encompasses a broad range of phenomena with noteworthy macroscopic features (e.g., a seizure) that are best understood by attention to the changing values of a collective variable (e.g., neuronal membrane voltages, neurotransmitter concentrations, their ratios and rates of release and of diffusion, blood flow and oxygen extraction) which allows spatio-temporal tracking of a "pattern resulting from the interactions among multiple elements in a system," and which may incorporate interactions with the environment.

Interpretation of changes in these variables and the clinical decisions stemming from said changes take into account certain other factors such number and type of neural components making up a network, its topology and cytoarchitectonic properties; the density, direction of connections, and number of synaptic "stations" (nodes and/or hubs depending on the scale at this they are studied);" their location in the brain; hierarchical standing; and functional dependency on state (e.g., wakefulness vs. sleep; attentive vs. relaxed, etc.); among others. Anatomo-functional information about these variables and factors may be obtained during passive (no tasks) or active/event related conditions (motor, sensory or cognitive tasks) using imaging and/or other electrophysiological, chemical, physical or cognitive "probes". Testing during passive or active states may be performed in-between, during, or immediately after seizures and also according to time of day, circadian rhythm, level of consciousness (awake vs. sleep), on vs. off medications, time elapsed from last seizure, severity of previous seizure(s), etc. Cognitive probes include, but are not limited to, simple or complex reaction time, visuo-spatial, language, or memory tasks.

Imaging probes include, but are not limited to magnetic resonance (MR), diffusion tensor magnetic resonance, MR tractography, MR spectroscopy, SPECT, PET, or near-infrared spectroscopy.

Electrophysiologic, physical, or chemical "probes" include but are not limited to non-invasive or invasive electroencephalography, magnetoencephalography, rheoencephalography, thermography, microdialysis, ion sensitive electrodes, neurotransmitter sensitive devices, pressure sensors, or ultrasound sensors.

Other useful "probes" are paired pulse stimulation, collision tests, transcranial magnetic or electrical stimulation, xenon enhanced computed tomography, dynamic perfusion computed tomography, MR dynamic susceptibility contrast, arterial spin labeling, or Doppler ultrasound.

Certain important anatomical details about the synaptic organization of brain networks (e.g., type (inhibitory or excitatory)) and their proportion, number of synapses and their location on neurons (e.g., dendrites or soma), presence of extra-synaptic receptors, presence or absence of projections between structures (e.g., nodes or hubs)) and their length and density, degree of coupling between nodes/hubs as a function of state (awake vs. asleep) are still evolving and some are the subject of dispute among neuroscientists. By way of example, there is a lack of correlation of results obtained through different mapping methods such as anatomical (e.g., Marchi technique) and electrophysiological (e.g., evoked responses) about the connectivity between component elements of neuro-anatomical networks and the pathways mediating visual, auditory, or somato-sensory responses recorded from the amygdaloid complex are unknown. This disclosure's central teachings rely (albeit not exclusively) on network theory as adapted herein to the study of brain behavior; its validity for certain applications is independent of certain details about its micro-, meso-, macro- or megascopic architecture or behavior and state-of the art pitfalls do not vitiate the usefulness and validity of this disclosure.

The different embodiments of this disclosure provide for prediction, early detection, prevention of spread or of emergence or blockage of seizures to be performed at one or more of the network(s)' structure(s) or their connection(s), either simultaneously or sequentially so as to bias or modulate said component(s) and/or alter functional or anatomical connectivity to ultimately decrease the probability of seizure emergence or spread. The therapies used herein may: a) Inhibit (pre-, post- or extra-synaptically) and/or dis-facilitate structures that promote seizure emergence; b) Dis-inhibit and/or excite structures that suppress seizure emergence; c) Depending on the dynamics at play, block/weaken and/or strengthen functional connectivity between nodes or hubs; d) Shunt or fractionate currents so at to divert from certain parts of a network to others in the same network or from a network to another, exploiting Kirchhoff's current or voltage laws.

The diffusion of electrical currents within the brain, which as vectors have both magnitude (potential) and direction, takes place at several spatial (active membrane sites, cells, columns and the cortical synergic groups) and/or temporal domains or scales, where they flow differentially through the lattice of intercellular spaces and through the network of neurons and glial cells. These flows occur through a large number of routes at their disposal, each route being the path for only a small part of the total current. This spatio-temporal "fractionation" or dispersion of electrical currents may be further enhanced to prevent spread or emergence of seizures by decreasing current densities spatially and or temporally to subthreshold (for the generation of action potentials) levels. This may be accomplished by reversible (e.g., chemical) or irreversible (e.g., tissue ablation), non-adaptive (pre-specified, state-independent) or adaptive (e.g., state-dependent) alterations to the excitability and/or conduction properties of neural tissue. For example, lowering the temperature of axons forming a pathway between two nodes, will slow down electrical impulse conduction and decrease current density/unit timed, making it sub-threshold and preventing the generation of action potentials. Similar effects may be achieved using chemical (e.g., drugs, osmotically active agents), electrical (e.g., anodal conduction block with gradual release so at to avoid the "rebound" phenomenon or mechanical (e.g., application of negative or positive pressure to alter membrane structure and with it neuronal activation or when appropriate, deactivation).

Neural tissue has fractal or multi-fractal properties; changes in these measures may be effected via physical (e.g., electrical, thermal) or chemical means (e.g., delivery of osmotically-active agents to a certain region) to fractionate/limit electrical currents or enhance their passage, depending on the site, state of the tissue of interest and the task at hand (e.g., inhibit, disinhibit, facilitate, disfacilitate said tissue). At a fundamental level, this approach, modifies diffusion limited aggregation growth probabilities of electrical currents to either increase or decrease the number of fractal heterogeneity of neural tissue to alter its conductivity or resistivity properties. An electric field is a multi-fractal measure, which underscores one of the central themes of this narrative, the spatio-temporal "non-uniformity" or heterogeneity of the interface formed by neuropil and a charged electrode surface and thus the usefulness (for optimization purposes) of application of concepts from multi-fractal theory, among others to characterize this complex phenomenon.

Inhibition, disinhibition, facilitation, or dis-facilitation may be exerted on structures that are inherently excitatory or inhibitory and that are part of the network where a seizure emerges or of a network that interacts with the network from where a seizure emerges. Inhibition, disinhibition, facilitation, or disfacilitation may be implemented in any temporal order to one or more structures in a network(s).

This disclosure may resort to collision of currents to prevent emergence or spread or seizures within or between networks. For example, if in a patient with seizures emerging in the left mesial temporal region, the anterior commissure serves as the main path of spread into the right mesial temporal region, detection of seizure onset on left may trigger a timely barrage of electrical impulses from the right mesial temporal region to the anterior commissure that will collide with those originating from the left, resulting in their annihilation, preventing their arrival into the right mesial temporal region and with it seizure spread.

In one or more embodiments, this disclosure applies theories and concepts such as inter-hemispheric rivalry and competitive feedback inhibition, neuronal oscillations that coordinate/bind cross-neuronal interactions, the universal control system theory, and neuronal network stabilization based on synaptic homeostasis.

In one embodiment, graph theory may be applied to the prediction, detection, or management of seizures and epilepsy and relevant concepts and terms may be used. Brain structures may be treated as "nodes" or "hubs" depending on the degree of connectivity and centrality and the spatial scale at which they are being regarded. For example, the hippocampus proper may be classified as a "hub" when the network of interest is the hippocampal formation or as a "node" if the limbic system is under consideration. The concept of "gates" and "gating" is also introduced so as to acknowledge and incorporate a dynamical hierarchy that weighs more heavily, functional roles than structural features. For example, learning, which requires formation of new memories, cannot materialize without the hippocampus, which "gates" all new verbal and visuo-spatial material, enabling the formation of a permanent record.

An element incorporated into the "systems network" approach that shapes this disclosure is the dependence of synchronization levels on network topology. For example, by making connections between two sides functionally sparse or feeble, seizure spread may be prevented or delayed; a similar result may obtained by making firing rates between two nodes or hubs, dissimilar. Also, by exploiting (e.g., strengthening) dynamic homeostasis, Hebbian behavior (which plays a role in epileptogenesis) is weakened, and with it, spread of abnormal activity. Default network (brain structures that are activated during the relaxed state or in the absence of a cognitive load) and central executive network regions (those supporting certain cognitive function necessary for adaptive behavior) (FIG. 13) are anti-correlated; that is, when one is active the other is inactive; this feature may be exploited to control or modulate epileptogenic regions that are under the control of one or of the other network. This anti-correlation may explain why inattention or being in a relaxed state facilitates the emergence of seizures in certain individuals.

In one embodiment, graph theoretical analysis will be applied to assess network functionality and estimate the probability of seizure emergence and/or spread for a given network(s). This will first entail the creation of n N×N (n=1 . . . nth) network matrix/matrices that will be populated with value measures such as synchronization, entropy, absolute or relative power at certain frequencies and its variance and/or its rate of change, as estimated between pairwise (i, j) combinations (in any possible permutation) of sensors (e.g, electrical, chemical, magnetic, optical, etc). These sensors may collect data from: a) cerebral sites that correspond to known networks such as the hippocampus proper, hippocampal formation, limbic system, central executive network, default mode network, cortico-spinal/pyramidal network, reticular activating network; b) pre-specified extra-cerebral networks such as the cardiac, respiratory, metabolic, musculo-skeletal; c) pathways such as the corona radiata, internal capsule, commissures, fasciculae, or tracts, or d) Non-network sites cerebrally or extra-cerebrally (referring to sites that are either not connected or remotely/weakly connected to a network(s) of interest). The next step in the process is to transform the matrix/matrices into a binary graph(s); a binary graph is made up of elements or "vertices"/"nodes" that in one embodiment of this disclosure correspond to sensors and/or connections/pathways ("edges") between vertices/nodes that may or may not represent actual anatomical connections; in one embodiment graph theory will be modified as follows: 1. Edges will have a value between 0-1 (not 0 or 1) and a pre-specified or adaptive threshold (T); this will allow more precise tracking of changes in connectivity strength between vertices as a function of level of consciousness, type and level of cognitive or other activities, etc., to better estimate probability of seizure emergence or spread within or between networks; 2. The edges will have direction of flow of information (e.g., electro-chemical impulses) so that a reversal in direction, if it occurs, may be used for the task at hand. Once a graph(s) has/have been "illustrated" it is characterized in terms of its size, connection density, proportion of reciprocal connections, degree distributions, diameter, radius, path length and/or, clustering coefficients. These properties may be quantified using standard graph theory methods know to those skilled in the art and tools such as those found in Matlab® (Mathworks, Natick, Mass.). The data obtained from a patient may be processed in real-time of off-line and along with existing knowledge (textbooks, scientific articles, etc.), may be used as needed to further define or refine: a) anatomical (type, pattern, density, fiber type, length, etc.) connections within and between networks; b) functional connectivity through identification and characterization of statistical dependencies (e.g. temporal correlations) between and within networks; c) effective connectivity by unraveling causal effects within and between networks using measures such as Grange causality. Network behavior/dynamics may be additionally characterized through; 1. Measures of functional segregation such as clustering, modularity and number/type of motifs; 2. Measures of functional integration such as path length or efficiency or, 3. Measures of functional influence such as centrality.

(As used herein, reversal in the direction of flow of impulses/information between nodes, hubs, or networks has two meanings: 1. In the case of reciprocal connections between nodes, if the information flow from node A to B has been historically greater than from B to A, a reversal occurs when the flow from B to A becomes greater than from A to B; 2. In the case of uni-directional connections, if the impulse flow is normally from node A to B (orthodromic), if the direction of flow is from B to A, (antidromic), this also constitutes a direction reversal).

Other measures that may be performed on-line or off-line to characterize brain networks include but are not limited to degree distributions, characteristic path lengths, modular structure and local clustering properties, degree centrality (an important node is involved in a large number of interactions), closeness centrality (an important node is typically "close" to, and can communicate quickly with, the other nodes in the network), betweenness centrality (an important node will lie on a high proportion of paths between other nodes in the network, or eigenvector centrality (an important node is connected to important neighbors). Other concepts of centrality that have been proposed and may be used in this disclosure are betweenness centrality and information centrality. Nodes or hubs may be ranked according to the effect their facilitation or inhibition has on the capacity or efficiency of a network in propagating information and the centrality measure based on game theoretic concepts as known to those skilled in the art.

The concept of "preferential attachment" will be exploited in this disclosure as needed, to determine preferred routes of spread and targets and to prevent or contain the seizure using for example: a) electrical stimulation or chemical compounds to reversibly inhibit, disinhibit, facilitate or disfacilitate neuronal ensembles or cause a conduction block; b) thermal means to depress or enhance neuronal activity or block or speed up impulse conduction along certain paths; c) ultrasound or some other form of disturbance (e.g., positive or negative pressure) to prevent the tissue from generating and/or conducting electrical impulses or to disrupt the release (into synaptic or extra-synaptic spaces) or re-uptake (into neurons or astrocytes) of ions or neuro-transmitters; d) motor, sensory, cognitive or autonomic activity to compete for processing resources and time with the abnormal (e.g., epileptogenic) activity.

Implicit in the network concept of seizure generation is the state-dependent contribution that other networks make to the emergence of seizures in the main epileptogenic network. It thus follows, that intervention at an inter-network scale may prevent seizure emergence by redirecting, fractionating or enhancing flow to reduce or revert an ictogenic or epileptogenic "potential gradient" to maintain an adaptive dynamic homeostasis. Dynamic homeostasis, as defined herein, is fundamentally different from Cannon's homeostasis which is a static concept and the one universally adopted.

Brain network topology may belong to a class known as "small world". In this class, the clustering coefficient is much greater than that of equivalent random controls $\gamma \gg \gamma random$ while their path lengths are comparable ($\lambda \approx \lambda random$). The small world index $\sigma sw$, is given by $\sigma sw = \gamma/\gamma random/\lambda/\lambda random$. The topology of small world network endows them ith high efficiency as information transfer is fast, occurring at relatively low energy costs. There may be other classes of brain networks such as power law distributed wherein the connectivity among the large majority of nodes is sparsely with a "handful" of hubs having exceedingly dense connectivity. Where exchange of information may take place more rapidly within a "power law" than a "small world" network, they are also more vulnerable to failure given their exceedingly high concentration of information into a few hubs. The relation between topology and function in networks is mentioned, to point out that reversible or irreversible intervention of therapies may be applied to the epileptic brain to prevent emergence or spread of seizures. The efficacy of surgical resection of mesial temporal lobe structures in controlling seizures may be the result of an irreversible topology-transforming intervention: extirpation of hubs (hippocampus and amygdala in this example) increase the effective connectivity among remaining nodes and hubs, increasing the rate of information transfer in an energetically cost-effective manner.

Embodiments of the present disclosure provide for determining a potential site of spread of epileptic electrical in the brain (e.g., an epileptic seizure) and providing a treatment. For example, an epileptic event may be detected in a first node of a patient's brain network. A determination may be made as to whether a second node of the patient's brain network may be affected by the activity of the first node. Based upon this determination, a treatment may be applied to the second node or its connections to prevent spread of the epileptic activity from the first to the second node.

Figure 1:
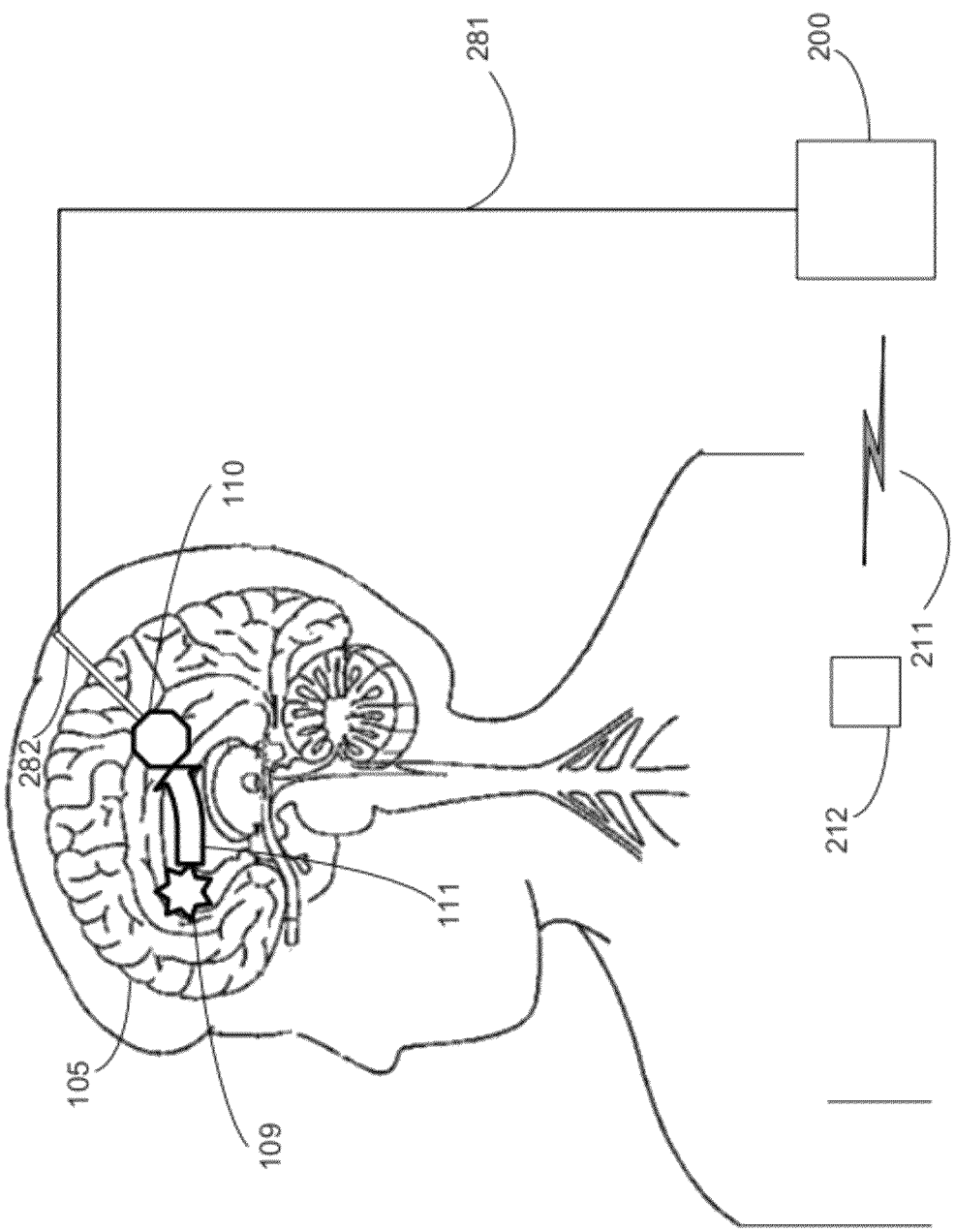

Turning now to FIG. 1, a stylized medical device system is depicted. The medical device system comprises a medical device 200 and at least one sensor 212.

In some embodiments, the medical device 200 may be implantable, while in other embodiments, such as that shown in FIG. 1, the medical device 200 may be completely external to the body of the patient.

The sensor 212 may be implanted in the patient's body, worn external to but in contact with the patient's body, or positioned in proximity to but not in contact with the patient's body. The sensor 212 may be configured to receive cardiac activity data, body movement data, responsiveness data, awareness data, or other data from the patient's body.

FIG. 1 depicts the medical device 200 being in wireless communication 211 with the at least one sensor 212. In other embodiments (not shown), the medical device 200 may be in communication with the at least one sensor 212 via a lead or other wired communication channel.

The medical device system shown in FIG. 1 also includes at least one electrode 282. In the depicted embodiment, the electrode 282 may be implanted in the patient's brain 105 such that the terminus of the electrode 282 may be in proximity to brain region 110. Herein, the terms "sensor," "electrode," and "probe" may be used interchangeably. Sensors/electrodes/probes may be used to record physical (e.g., electrical, thermal, force/unit area or pressure), chemical (e.g., ions, neurotransmitters, O2), or cognitive (e.g., attention, memory, language, comprehension) signals, among others.

Two brain regions 109, 110 are depicted in FIG. 1. Brain region 109 may be considered a first node of a neural network, and brain region 110 may be considered a second node of the neural network. A nodal connection 111 between the brain regions 109, 110 is represented with an arrow in FIG. 1.

The term "neural network" is used herein to refer to natural, non-artificial networks comprising a plurality of neurons assembled into nuclei or structures (nodes or hubs) connected via fibers, pathways, or comissures (edges). The difference between nuclei, structures, or regions referred herein as nodes or hubs is one of connectivity, centrality, functional hierarchy being lower in the former compared to the latter. In line with this and depending on the network scale at which this disclosure is being applied, a structure may be classified as a node in a network of a certain size and hub in a sub-network of said network. For example the hippocampal formation is a sub-network of the limbic network. Biological networks may include neural networks and those which while not neural, are under neural control. For example, the brain and heart form a network; the various central structures with autonomic functions such as the hypothalamus and insula are nodes or hubs, connected to the heart via the vagus nerve and the inter-medio lateral columns, acting as edges.

Exemplary neural networks of the brain include, but are not limited to, sensory networks, motor networks, or cognitive networks.

In one embodiment, the neural network of interest in the present disclosure is a limbic system, and said first node and said second node are selected from an amygdala, a hippocampus, a dentate gyms, a subiculum, an entorhinal cortex, an anterior thalamic nucleus, a mammillary body, a cingulate gyms, an anterior commissure, a fornix, an arcuate fasciculus, a temporal stem, an orbito-frontal cortex, a locus coeruleus, a reticular thalamic nucleus, a caudate nucleus, a striate nucleus, or a ventral tegmental nucleus.

It must be borne in mind that connections between neurons, and between regions of the brain, may have different weightings and that these weightings are not only determined by anatomical properties (e.g., number and type of fibers connecting two regions) but also by the functional state of the network and of the patient. That is, a neuron or a brain region may weight signals received from a first upstream/downstream brain region more heavily or more lightly than signals received from a second upstream/downstream brain region.

Also, connections between neurons/brain regions may be asymmetrical. That is, a downstream brain region may weight signals received from an upstream brain region more heavily than the upstream neuron/brain region weights signals received from the downstream neuron/brain region.

Further, the weights of connections between neurons/brain regions are not necessarily proportional to the distance between the neurons/brain regions. That is, neurons/brain regions in proximity to one another may have less influence on and/or be less influenced by anatomically nearby neurons/brain regions than distant neurons/brain regions to which they are nodally connected.

Inherent to the detection of an epileptic event is the fact one is already occurring. All that can be done at that point is to block its spread, which will lead to their relatively rapid termination since seizures confined to a given region are self-limited, their duration being somewhat proportional to the volume of tissue engulfed by said activity: the smaller the epileptogenic area the shorter the seizure's duration. Spread can take place between nodes or hubs within a network or, considering neural networks at large scales, between neural networks. If an epileptic event emerges in a central hub of a neural network, the probability of spread to many or all nodes connected to it is high and the probability of spread to other networks is equally high, if the epileptogenic hub is connected to a hub in the other network. If an epileptic event emerges in a node within a neural network, the possibility of spread depends on proximity and connectivity of that node to others in its network, to a hub of its network, and/or to other neural networks, the functional state of the network and of the patient.

Brain region 109 may be a node, hub or network from where a seizure emerges. Brain region 110 may be a node, hub or network of that patient from where epileptic events typically do not emerge. However, upon emergence of an epileptic event in brain region 109, which is connected to region 111 may spread/propagate to brain region 110, lengthening its duration and severity.

Two or more electrodes 282 may be implanted in the patient's brain (not shown). If multiple electrodes 282 are implanted in the patient's brain, they may be implanted such that their termini are in proximity to one or more brain regions 110 (not shown). For example, in such an embodiment, the electrode(s) 282 may be implanted such that two or more electrode termini are in proximity to a single brain region. Alternatively, electrode(s) 282 may be implanted such that each brain region of interest is in proximity to the terminus of a single electrode.

Also, FIG. 1 depicts the medical device 200 being in communication with the electrode 282 via a lead 281. In other embodiments (not shown), the medical device 200 may be in wireless communication 281 with the electrode 282, or in communication using a wired communication channel other than a lead.

Figure 2:
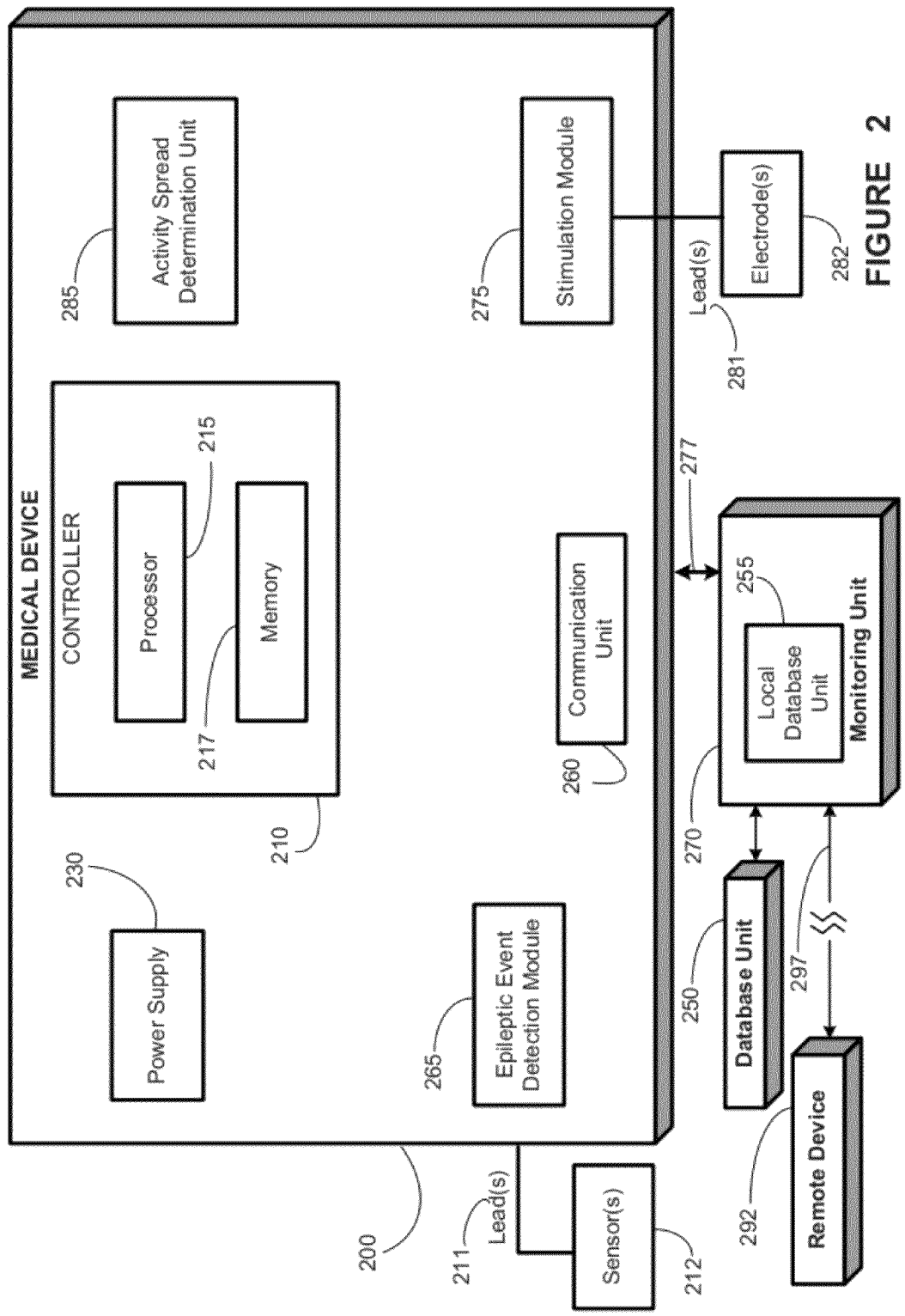

FIG. 2 presents a block diagram of a medical device system, in accordance with one illustrative embodiment of the present disclosure.

The medical device 200 may comprise a controller 210 capable of controlling various aspects of the operation of the medical device 200. The controller 210 may be capable of receiving internal data or external data, and in one embodiment, may be capable of causing a therapy module 275 to generate and deliver a therapy (e.g., an electrical signal) to target tissues of the patient's body for treating a medical condition. For example, the controller 210 may receive manual instructions from an operator externally, or may cause a therapy to be generated and delivered based on internal calculations and programming. The controller 210 may be capable of affecting substantially all functions of the medical device 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM), dynamic random access memory (DRAM), electrically erasable programmable read-only memory (EEPROM), flash memory, etc.

In other embodiments, one or more electrode(s) 282 may be adapted to be coupled to at least one of a portion of a brain structure of the patient, a cranial nerve of a patient, a spinal cord of a patient, a sympathetic nerve structure of the patient, or a peripheral nerve of the patient.

The medical device 200 may also comprise a power supply 230. The power supply 230 may comprise a battery, voltage regulators, capacitors, etc., to provide power for the operation of the medical device 200, including delivering a therapeutic electrical signal. The power supply 230 comprises a power source that in some embodiments may be rechargeable. In other embodiments, a non-rechargeable power source may be used. The power supply 230 provides power for the operation of the medical device 200, including electronic operations and the electrical signal generation and delivery functions. The power supply 230 may comprise a lithium/thionyl chloride cell or a lithium/carbon monofluoride (LiCFx) cell if the medical device 200 is implantable, or may comprise conventional watch or 9V batteries for external (i.e., non-implantable) embodiments. Other battery types known in the art of medical devices may also be used.

The medical device 200 may also comprise a communication unit 260 capable of facilitating communications between the medical device 200 and various devices. In particular, the communication unit 260 may be capable of providing transmission and reception of electronic signals to and from an monitoring unit 270, such as a handheld computer or PDA that can communicate with the medical device 200 wirelessly or by cable. The communication unit 260 may include hardware, software, firmware, or any combination thereof.

The medical device 200 may also comprise one or more sensor(s) 212 coupled via sensor lead(s) 211 to the medical device 200. Sensor(s) 212 are capable of collecting one or more body signals from a patient's body. Exemplary body signals include, but are not limited to, those related to an autonomic index, such as the patient's heart beat, blood pressure, and/or temperature, among others, and/or signals related to a neurologic index such as responsiveness, memory, visuo-spatial function, or body movements. In one embodiment, the sensor(s) 212 may be the same as electrode (s) 282. In other embodiments, the sensor(s) 212 are separate structures that may be placed on the patient's skin, such as over the patient's heart or elsewhere on the patient's torso. The sensor(s) 212 and accompanying leads may be considered an interface for the medical device 200 to receive at least one of autonomic data, neurologic data, or other data.

In a particular embodiment, the sensor(s) 212 may be configured to collect one or more electrical signals from a patient's brain, such as may be collected by electroencephalography (EEG), electrocorticography (ECoG), or the like.

More information on body signals, such as cardiac signals, respiratory signals, body movement signals, skin resistance signals, responsiveness signals, and awareness signals, as well as techniques and devices for the acquisition thereof, is provided by U.S. patent application Ser. No. 12/896,525, filed Oct. 1, 2010, which is incorporated herein by reference in its entirety.

The medical device may also comprise an epileptic event detection module 265. The epileptic event detection module 265 may be configured to detect an epileptic event in a neural network where the epileptic event emerges. In one embodiment, detecting an epileptic event in a first node or hub in a neural network where the epileptic event emerges may be based on electrical signals collected from the patient's brain. In another embodiment, detecting the epileptic event may be based on sensed body signals other than electrical signals collected from the patient's brain.

More information regarding detection of epileptic events from sensed body signals, and determination of severity and location in the body of epileptic events, can be found in U.S. patent application Ser. No. 12/756,065, filed Apr. 7, 2010; U.S. patent application Ser. No. 12/770,562, filed Apr. 29, 2010; U.S. patent application Ser. No. 12/896,525, filed Oct. 1, 2010; U.S. patent application Ser. No. 13/040,996, filed Mar. 4, 2011; U.S. patent application Ser. No. 13/091,033, filed Apr. 20, 2011; and U.S. patent application Ser. No. 13/098,262, filed Apr. 29, 2011; all of which are hereby incorporated herein by reference in their entirety.

As stated above, in one embodiment, the medical device 200 may also comprise a therapy module 275 configured to deliver at least one therapy, such as electrical signals generated by module 275 and delivered to one or more electrodes 282 via one or more leads 281. Electrical therapy may be delivered to the electrode(s) 282 by the therapy module 275 based upon instructions from the controller 210. The therapy module 275 may comprise various components. In one embodiment, the therapy module 275 delivers electrical therapy, and comprises circuitry, such as electrical signal generators, impedance control circuitry to control the impedance "seen" by the leads, and other circuitry that receives instructions relating to the delivery of the electrical signal to tissue. The therapy module 275 may be capable of delivering electrical signals over the leads 281 to the electrode(s) 282.

Electrical therapy is not the only therapy that may be applied by therapy module 275. In one embodiment, the therapy is a thermal therapy, a drug therapy, an endosomatic therapy (e.g., therapies that exploit the patient's body's or brain's natural mechanisms) such as engaging the patient's attention for performance of cognitive, motor or sensory tasks. The endosomatic activity competes with the abnormal activity (e.g., epileptic) for "resting" neurons decreasing the probability of spread. If the network at risk for epileptic invasion is for example, the somato-sensory cortex representing a patient's right hand, and the first seizure manifestation (tingling) is in the right thumb, engagement of the other four fingers by sensory stimulation may prevent the spread of epileptic activity into the cortical area that represent them. Other therapies may be supportive, optical, acoustic, or two or more thereof.

Whatever the therapeutic modality, the therapy module 275 may be configured to apply a therapy to at least one neural network/structure of the patient. In one embodiment, that neural structure may be a second hub or node in the neural network, based on an indication of an epileptic event in the first hub or node in the neural network. Applying the therapy may be performed prior to the spread of the epileptic event to the second node, and/or upon detecting an indication of the epileptic event spreading or having spread to the second node.

Alternatively or in addition, a therapy may be applied to a neural structure outside said neural network, in response to detecting said epileptic event. For example, a therapy may be directly applied to a network connected to it, or indirectly via cranial nerve (e.g., a vagus nerve), a region/node of a spinal cord, or a peripheral nerve.

Alternatively or in addition, a therapy may be applied to multiple neural structures of the patient, multiple sites within a single neural structure/network.

Applying a therapy to a neural structure, such as the second hub or node, may be direct or indirect. For an example of indirect application, in one embodiment, applying the therapy to the second node may be accomplished by applying the therapy to the first hub or node, in view of the relatively high and/or important connectivity presumed to exist between the first hub or node and any hub or node to which it may spread, e.g. the second hub or node. In other words, the first node may be considered a connection to the second node.

Also, applying a therapy to a neural structure may not be limited (due to connectivity) to only a portion of that structure. For example, if the limbic system is considered a network and the amygdala a node within it, an electrode or probe implanted within and configured to deliver a therapy electrical stimulation to the amygdala would be applying a therapy to the network, in this example, the limbic system. For another example, applying a therapy to the vagus nerve at a location in the neck is an application of therapy to a neural structure comprising the vagus nerve; the dorsal motor nucleus of the vagus, the nucleus ambiguus, and the solitary nucleus of the brain; and neural networks connected to one or more of those nuclei.

The electrical stimulation pulse may comprise a plurality of parameters, such as waveform, pulse width, amplitude, phase, or frequency, among others.

The medical device 200 may also comprise an activity spread determination module 285. The activity spread determination module 285 may be configured to do one or more of the following: identify a second node or hub of said neural network, susceptible to invasion by said activity, based at least in part on at least one "information" (e.g., coupling or synchronization) measure between said first node and said second node and based on the behavior history and present functional state, estimate a probability of spread of said epileptic event to said second node and provide an action based on said probability value. The activity spread determination module 285 may be configured to identify, detect, estimate, or determine the likely of spread (or of emergence of abnormal activity) based on one or more local (e.g., an epileptogenic network) or global (e.g., brain or body) factors.

In one embodiment, the probability of spread from one node or hub to another within a network or between networks may be estimated from at least one of present and/or past information about: a rate of increase of seizure energy in one or more oscillation frequencies, an intensity of said epileptic event, a duration of said epileptic event, a length of fibers connecting said first node and second node, a number of synapses between said first node and said second node, a synaptic density between said first node and said second node, at least one conductivity property of fibers connecting said first node and said second node, a fiber density between said first node and said second node, a functional hierarchy level of at least one of said first node or said second node, a clinical hierarchy level of at least one of said first node or said second node, a degree of epileptogenicity associated with at least one of said first and said second node, an anatomical location in said network of said first node, an anatomical location in said network of said second node, a degree of functional connectivity/coupling between the second node and the first node, a type of connectivity (inhibitory or excitatory) between the second node and the first node, a plasticity of said neural network, an extent and ease of network recruitment within said neural network, a functional role of the second node, a topology of the network containing the first node, a topology of the network containing the second node, a state of the first node and its network, a state of the second node and its network, a number of nodes impacted by said epileptic event, a magnitude of spread, a rate of spread, a type of sub-network comprising at least one of said first node or said second node, or a number of sub-networks comprising at least one of said first node or said second node.

As used herein, "synaptic density" refers to the number of synaptic sub-elements per membrane unit area. Also, "fiber density" refers to the number of fibers per cross section unit area. "Synaptic target" refers to which part of the downstream neuron is the target of a synapse, e.g. soma, axon, or dendrite. The "degree of connectivity" refers to the number of nodes to which a node or hub are connected. "Epileptogenicity" relates to the ability of an area to entrain others in an epileptic event, including how many other areas and how often they may be entrained. "Type of connectivity" refers to whether activity by the first node inhibits, disinhibits, facilitates, or disfacilitates activity on the second node.

Anatomical connectivity can generally be considered fixed, although the recruitment of new nodes and connections (e.g., axonal sprouting) within the first node and the second node or between them may occur over long time scales. Functional connectivity is dependent on the state of the patient and/or the network of interest in the patient's brain (e.g., level of consciousness (awake or asleep), type of cognitive task, if any, physical activity level (sedentary or exercising), body posture (standing up or sitting down), and/or metabolic state (hypo/normo/hyperglycemia, hypoxia/, etc.). Functional connectivity reflects short term network plasticity, i.e., the weights of connections within the network may change rapidly with changes in state. As should be apparent, a coupling characteristic, indication of epileptic activity spread, estimated proclivity, or determined probability can be dynamic, dependent on states of nodes and the connectivity between them.

In one embodiment, the coupling characteristic, indication of epileptic activity spread, estimated proclivity, or determined probability may be selected or determined from at least one of: a time elapsed since a prior epileptic event, a seizure severity index of a prior epileptic event, a burden of a prior epileptic event, an impact of a prior epileptic event, the likelihood of impact of the epileptic event on a neurological function of the patient, a time elapsed since a therapy for a prior epileptic event, a type of a therapy for a prior epileptic event, a response to a therapy for a prior epileptic event, a physical and/or cognitive state of the patient at the time of said detecting, a time of day at the time of said detecting, an empirical estimation of epileptic event spread from the first node at the time of said detecting, or a history of epileptic event spread in at least one of said patient or a patient population with relevant characteristics similar to said patient.

In one embodiment, the coupling characteristic, indication of epileptic activity spread, estimated proclivity, or determined probability may be selected or determined from at least one of: an autonomic index indicative of a probability of epileptic event spread from the first node, a neurologic index indicative of a probability of epileptic event spread from the first node, a metabolic index indicative of a probability of epileptic event spread from the first node, an endocrine index indicative of a probability of epileptic event spread from the first node, a tissue stress marker index indicative of a probability of epileptic event spread from the first node, a physical fitness index indicative of a probability of epileptic event spread from the first node, a body integrity index indicative of a probability of epileptic event spread from the first node, a quality of life index indicative of a probability of epileptic event spread from the first node, a seizure burden index indicative of a probability of epileptic event spread from the first node, or a number of indices indicative of a probability of epileptic event spread from the first node.

A more detailed description of the activity spread determination module 285 is provided in FIG. 4 and accompanying description below.

The medical device system of FIG. 2 may also comprise a monitoring unit 270, which may be a device that may be capable of transmitting and receiving data to and from the medical device 200. In one embodiment, the monitoring unit 270 may be a computer system capable of executing a data-acquisition program. The monitoring unit 270 may be controlled by a healthcare provider, such as a physician, at a base station in, for example, a doctor's office. In alternative embodiments, the monitoring unit 270 may be controlled by a patient in a system providing less interactive communication with the medical device 200 than another monitoring unit 270 controlled by a healthcare provider. Whether controlled by the patient or by a healthcare provider, the monitoring unit 270 may be a computer, preferably a handheld computer or PDA, but may alternatively comprise any other device that may be capable of electronic communications and programming, e.g., hand-held computer system, a PC computer system, a laptop computer system, a server, a personal digital assistant (PDA), an Apple-based computer system, a cellular telephone, etc. The monitoring unit 270 may download various parameters and program software into the medical device 200 for programming the operation of the medical device, and may also receive and upload various status conditions and other data from the medical device 200. Communications between the monitoring unit 270 and the communication unit 260 in the medical device 200 may occur via a wireless or other type of communication, represented generally by line 277 in FIG. 1.

In one embodiment, the monitoring unit 270 may comprise a local database unit 255. Optionally or alternatively, the monitoring unit 270 may also be coupled to a database unit 250, which may be separate from monitoring unit 270 (e.g., a centralized database wirelessly linked to a handheld monitoring unit 270). The database unit 250 and/or the local database unit 255 are capable of storing various patient data. These data may comprise patient data acquired from a patient's body or brain, therapy parameter data, seizure severity data, and/or therapeutic efficacy data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions (e.g., programming parameters for a responsive therapy and/or setting references for one or more detection parameters) using the monitoring unit 270, which may include obtaining and/or analyzing data from the medical device 200 and/or data from the database unit 250 and/or the local database unit 255. The database unit 250 and/or the local database unit 255 may store various patient data.

One or more of the blocks illustrated in the block diagram of the medical device 200 in FIG. 2 may comprise hardware units, software units, firmware units, or any combination thereof. Additionally, one or more blocks illustrated in FIG. 2 may be combined with other blocks, which may represent circuit hardware units, software algorithms, etc. Additionally, any number of the circuitry or software units associated with the various blocks illustrated in FIG. 2 may be combined into a programmable device, such as a field programmable gate array, an ASIC device, etc.

Figure 3:
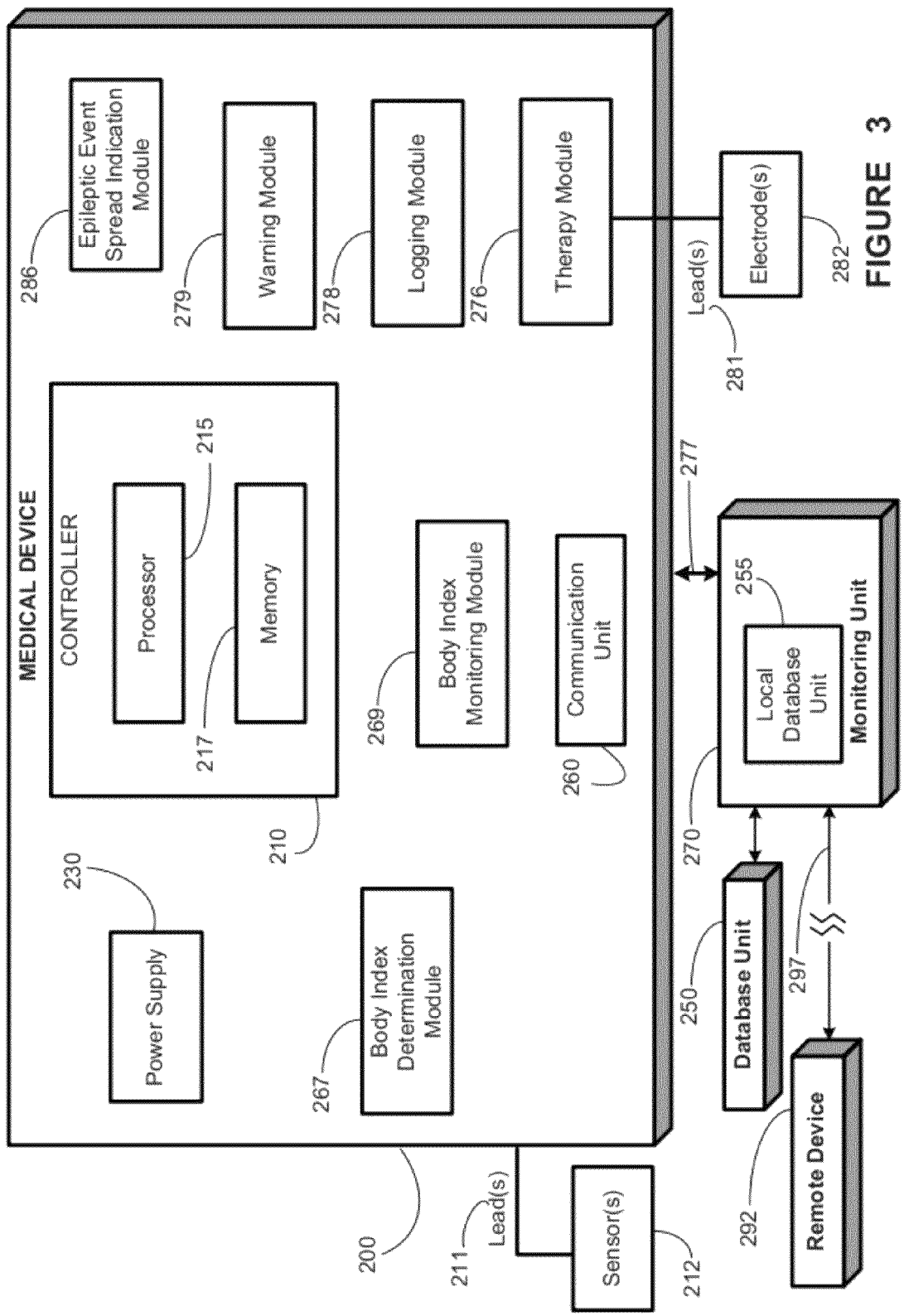

FIG. 3 presents a block diagram of a medical device system, in accordance with one illustrative embodiment of the present disclosure. FIG. 3 contains numerous elements in common with or substantially similar to those of FIG. 2, and such common/similar elements need not be discussed further.

The medical device 200 of FIG. 3 may comprise a body index determination module 267. The body index determination module 267 may be configured to determine at least a first body index indicative of an epileptic activity from at least one body signal collected by the sensor(s) 212. For example, the first body index may be a cardiac index, such as HR, HRV, or EKG complex morphology, among others. An indication of epileptic activity may be an increase in HR or a change in the shape of a PQRST complex among others.

The medical device 200 may comprise a body index monitoring module 269, which may be configured to monitor a second body index different from the first body index. For example the second body index may be a motor activity index, such as an amplitude, direction, or force of a body movement, among others.

The medical device 200 may also comprise an epileptic event spread indication module 286, which may be configured to detect an indication of epileptic activity spread, based upon at least one of the first body index or the second body index. For example, if the first body index is a cardiac index indicating an epileptic activity (such as by showing an increase in HR), then it may be known from prior patient data that the patient is having epileptic activity in a first node of a neural network within his/her brain. The second body index may be a motor activity index. If monitoring the motor activity reveals an indication of a fall, an abnormal body movement, or the like, then it may be known from prior patient data that the epileptic activity has spread to a second node of a neural network.

The epileptic event spread indication module 286 may be configured to quantify the probability, extent and/or direction of epileptic event spread. The epileptic event spread indication module 286 may be configured to determine the duration and/or severity of epileptic event spread.

The epileptic event spread indication module 286 may issue an indication which may be a basis for further action by one or more responsive modules, or may be stored, such as in memory 217, local database unit 255, database unit 250, remote device 292, or two or more thereof.

The medical device 200 may comprise one or more responsive modules, such as a therapy module 276, a logging module 278, or a warning module 279. The therapy module 276 may be configured to deliver a therapy to at least one neural structure network of the patient. The therapy may be an electrical stimulation therapy, as described elsewhere herein. Alternatively or in addition, the therapy may be one or more of a thermal therapy, a chemical therapy, a cognitive or a mechanical (e.g., negative or positive pressure to a network node, hub, or edge) therapy, among others.

In a particular embodiment, the therapy module 276 may be configured to apply a first therapy to a first neural structure/network of the patient for preventing spread of the epileptic event and/or configured to apply a second therapy to a second neural structure of the patient for preventing spread of the epileptic event.

The logging module 278 may be configured to log an indication of epileptic event spread. The warning module 279 may be configured to warn the patient, a caregiver, or a medical professional of the indication. For example, the warning module 279 may allow the patient to cease an activity, such as driving a car, bathing, swimming, or the like, that may be contraindicated by spread of the epileptic event to the second brain region.

Figure 4:
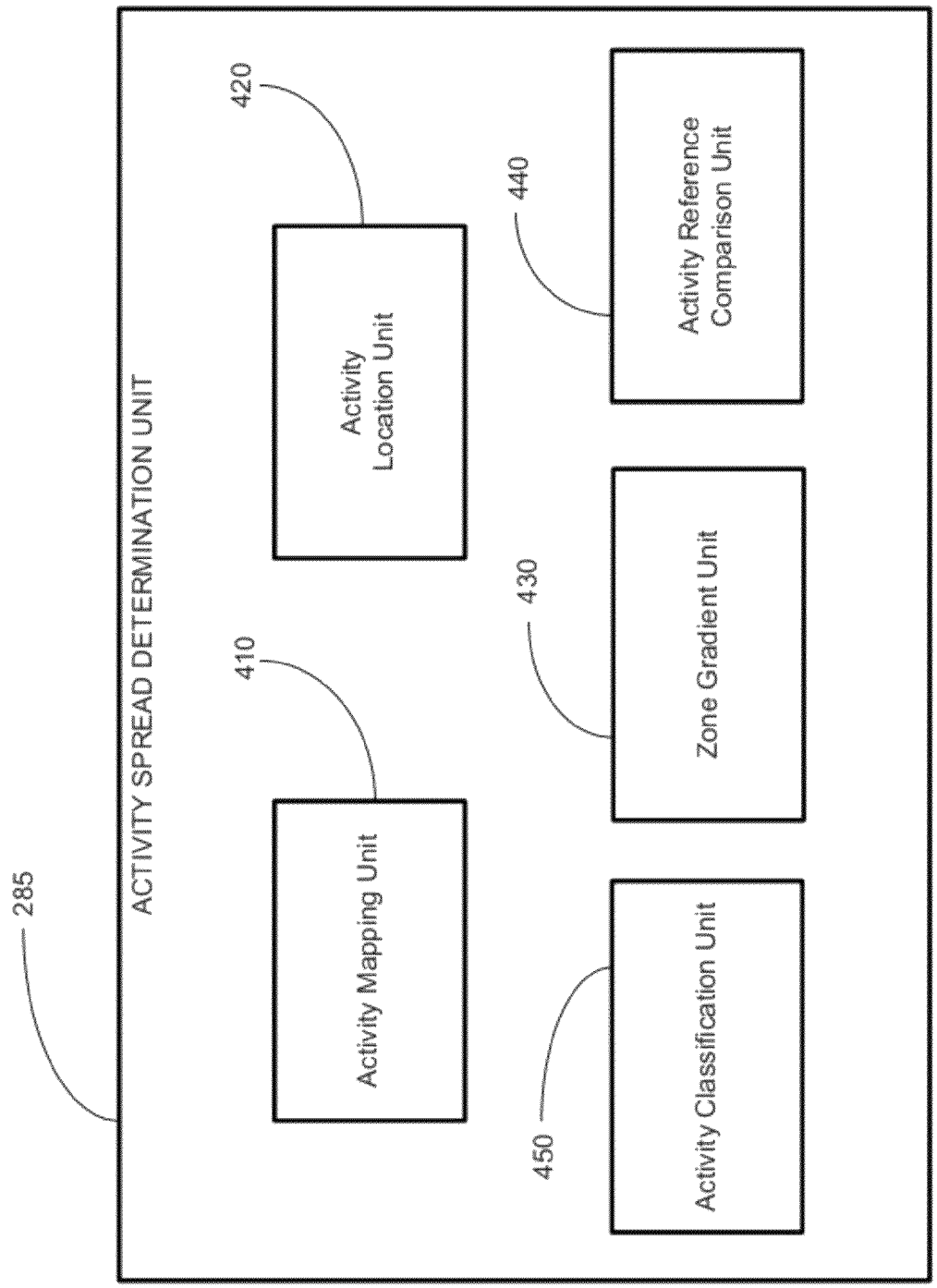
FIG. 4 shows a block diagram depiction of an electrical activity spread determination module of FIG. 3, in accordance with one illustrative embodiment of the present disclosure.

Turning now to FIG. 4, a stylized block diagram depiction of the activity spread determination module 285, in accordance with one embodiment of the present disclosure is illustrated. The activity spread determination module 285 may comprise an activity mapping unit 410, an activity location unit 420, a zone gradient unit 430, an activity reference comparison unit 440, and an activity classification unit 450. The activity that may be mapped, located, subjected to reference comparison, and/or classified by the activity spread determination module 285 may be one or more of an electrical activity, a magnetic activity, an extracerebral activity, a hemodynamic activity, a chemical activity, or a metabolic activity.

The activity spread determination module 285 is capable of determining a probability, or estimating the likelihood, of spread of a detected electrical epileptic activity (e.g., spread of an epileptic seizure) from one location/network in the patient's brain to another. In one embodiment, the module 285 may utilize various data, such as predicted gradient data of an electrical activity, a classification of an electrical activity, and/or a reference comparison of an electrical activity, in order to determine the probability of a spread.

The determination of an activity spread performed by the module 285 may encompass analysis of various components relating to, e.g., electrical activity in a patient's brain. A quotient that may provide information regarding the probability of extent of spread of epileptic activity (and/or severity) in the brain, i.e., a "spread quotient," may be determined. As an example, the spread quotient may provide information related to at least one of a probability of a spread of said epileptic activity, a speed of said spread of said epileptic activity, a direction of said spread of said epileptic event, an intensity of said epileptic activity, a duration of said epileptic and an extent, or a degree of network recruitment. Utilizing the spread quotient, therapy may be strategically applied to diminish the probability of spread and/or the extent and severity of any spreading epileptic activity. For example, applying a therapy, such as to the second node or hub of the neural network where the seizure emerged or to a node or hub in structure/network coupled to the network of seizure emergence, may be based at least in part upon the spread quotient.

In one embodiment, the spread quotient may be quantified as the number of nodes/hubs to which an epileptic event has spread, divided by the product of the number of nodes/hubs to which the epileptic event could have spread and the number of nodes/hubs of emergence of the epileptic event. More complex quantification of the spread quotient may involve a weighting of each node based on the proclivity of spread from a node to others, with higher weighting for spread to other nodes/hubs in other networks than for spread within the network of emergence, the hierarchy of the node if in the same network, or the hierarchy of networks in the case of inter-network spread. The hierarchy of networks may depend on the patient's state (wake or asleep, attentive or relaxed, lying down/standing up; driving/non driving), among other factors. The numerator in the spread quotient expression may be determined directly from EEG, ECoG, MEG or other measures of brain or cranial nerve electrical activity or functional MR, or indirectly using autonomic (e.g. HR, HRV, and/or activity) which may reveal to which nodes within a neural network or in the brain the epileptic event may have spread. One of the terms (number of nodes/hubs where the seizure emerged) of the spread quotient's denominator may be determined as the numerator, and the other (number of nodes/hubs to which epileptic activity could have spread) from the anatomy of the network.

In another embodiment, the spread quotient may be quantified as the number of nodes to which the epileptic event has spread, divided by the number of nodes monitored by the clinician.

The spread quotient may have other quantitative or qualitative definitions. The spread quotient may comprise various components, such as an intensity-level factor relating to an electrical activity that may result due to the spread of a detected electrical activity, the location of the possible spread of electrical activity, and/or the direction of the spread of electrical activity. These components may be factored, normalized, and/or otherwise mathematically manipulated to formulate the spread quotient. The spread quotient may be quantified to have various values that are indicative of various "weights" given to intensity, direction of a spread and/or a probability of spread of an electrical activity. Those skilled in the art, having benefit of the present disclosure may include other components into the calculation of a spread quotient and remain within the spirit and scope of the present disclosure.

Figure 5:
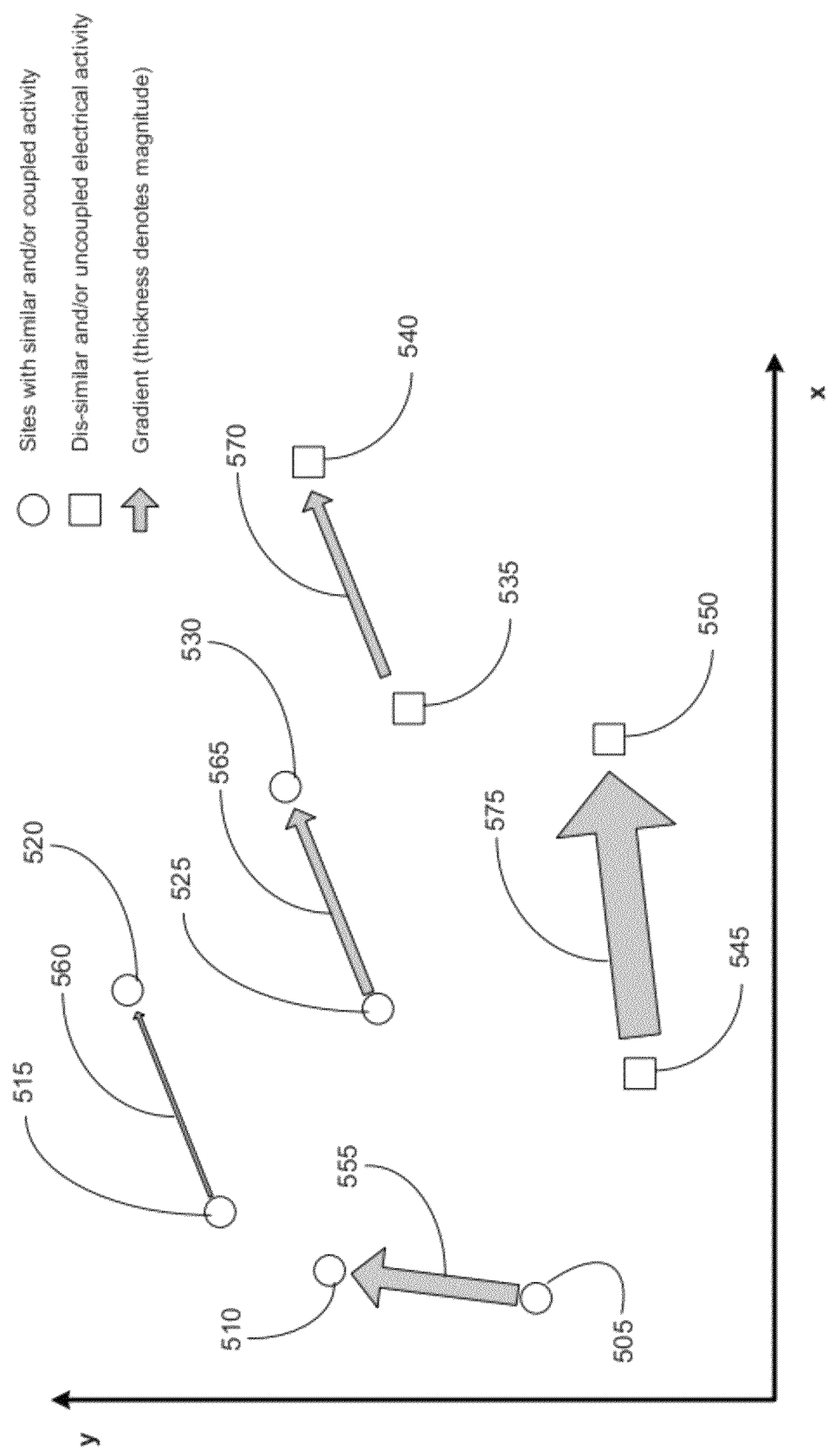
FIG. 5 shows a stylized depiction of a two-dimensional reference spread mapping and of a real-time mapping of electrical activities in a patient's brain, in accordance with one illustrative embodiment of the present disclosure.

The module 285 may determine a spread quotient relating to one or more activities in a patient's brain. The spread quotient may be utilized by the medical device 200 and/or a healthcare professional to identify and implement an action to the possibility of epileptic event spread. The activity mapping unit 410 is capable of mapping various activities (e.g., electrical, magnetic, hemodynamic, chemical, metabolic) in a patient's brain. The mapping may be based upon prior data, reference data and/or real-time or near real-time data. In one example, the activity mapping unit 410 may be used generate a two- or higher dimensional mapping of a patient's brain activity as shown in FIG. 4 (described in further details below). Brain electrical and magnetic activity refers to that generated by the flow of currents (sinks and sources across neural cell membranes); chemical activity refers to neurotransmitters and ions; metabolic activity to the utilization of energy compounds and their substrates and metabolites and hemodynamic activity to blood flow and gas exchanges between tissue and capillaries. These activities may be measured using various techniques, known to those skilled in the art. In one embodiment, extra-cerebral activities defined as those that may be measured without placing sensors on/inside the cranium or without aiming probes such as MR or optical sensors at the head, may be also used to determine extent and direction of spread of seizure activity. These include but are not limited to: a) Cognitive (e.g., attention, language, memory); b) Kinetic (e.g., eye movements, limb movements, body posture); c) Autonomic (e.g., cardio-respiratory), which are anatomically represented in and controlled by the brain, a fact that allows indirect tracking of epileptic activity. FIG. 5, described later, illustrates a stylized depiction of a three-dimensional mapping of electrical activity in a patient's brain.

Continuing referring to FIG. 4, the zone gradient unit 430 may determine any gradient associated with any detected electrical, chemical or metabolic activity. As such, these activities' paths may be mapped or predicted based upon the magnitude and direction of a gradient. The gradient unit 430 may use data from the activity mapping unit 410 and/or the activity location unit 420 to determine a magnitude of a gradient associated with the activity in one node/hub inside a network in reference to other nodes/hubs in the same network or in reference to other networks. In this manner, the spread and/or the movement of activity in the patient's brain may be predicted; the inherently high positive correlation between electrical, chemical, metabolic, and hemodynamic activities allows the drawing of inferences about the behavior of one based on that of others. For the sake of simplicity and brevity only electrical activities have been discussed in detail, keeping in mind the generalizability of said discussion to the chemical, metabolic, hemodynamic, and other activities.

Based upon information from the activity mapping unit 410, the activity spread determination module 285 may retrieve data and calculate or otherwise determine a gradient related to the detected activity; the gradient may correspond to power in a frequency band, phase of oscillations, ionic concentrations and/or flow rate, neurotransmitter concentrations and or release, flow or uptake rate, energy substrate concentrations, or temperature or blood flow (volume, rate), among others. The module 285 may also perform a classification of activity and/or classification of the reference comparison results of an activity. For example, based upon the activity mapping unit data, the activity location unit 420 may determine the probable location of another activity that may be coupled to the originally detected activity, and/or may also determine the location of the potential spread of activity. Data from the zone gradient unit 430 may be also utilized by the activity location unit 420 to determine in which direction a potential spread of activity may take place and/or determine the likely location of another activity that is related and/or caused by the originally detected activity.

In one embodiment, data from the activity mapping unit may 410 be utilized by the activity classification unit 450 to classify the type of seizure that is detected. To accomplish this, the node/hub, the network, their sizes and topologies, connectivities, functional hierarchy and roles are identified (e.g., a seizure may emerge in the left pes hippocampus which encodes memories and forms part of the hippocampal formation which is embedded in the limbic network which also regulates autonomic and endocrine functions, among others) and extra-cerebrally recorded indices such as reaction time, postural tone, body movements, heart and respiratory rates and patterns, their morphology, metabolic indices such as arterial pH and electrolytes, endocrine indices such as prolactin, to form a seizure composite that provides more relevant and complete information that the International Classification which electrographically (e.g., EEG) is based on the extent to which seizure activity is seen on the scalp (a seizure is classified as generalized if the abnormal activity appears simultaneously on both sides of the head, or partial if it comprises only a part of the head such as the left frontal head region) and clinically on level of consciousness (awake vs. unconscious) and if awake whether the subject remains aware during the seizure (simple partial) or losses awareness (complex partial). While useful, this classification has important limitations inherent to the recording modality (electrical sensors only placed on the scalp) and the lack of detailed and clinically informative phenomenology which would allow more precise and thorough correlations between the clinical manifestations and the spatio-temporal electro-chemical and hemodynamic changes that characterize seizures.

The seizure classification obtainable through this disclosure, may expand the known classes (e.g., generalized vs. partial and for partial, simple vs. complex), to include other observable in a quantitative manner. For example, in the case of a patient with seizures characterized by: a) an unprovoked expression of fear without increase motor activity but with tachycardia (peak heart rate: 135 beats/min with reference/non-seizure mean heart rate of 82); with reversible 2 mm. S-T depression (reference EKG: normal) and blood pressure (BP) elevation (BP of 138/89 vs. reference non-seizure BP of 112/70), hyperventilation (peak respiratory rate: 21 breaths/min with reference/non-seizure mean respiratory rate of 10 breaths/min.); b) loss of awareness as ascertained using a complex reaction time test, (patient failed test 28 s. after clinical onset (no failure during non-seizure state) and remained impaired compared to reference/non-seizure reaction time values for 45 min, after termination the abnormal electrical activity); c) motionless late in the course of the seizure (accelerometer register no motion in the standing position for 65 s. compared to 10 sec. for reference/non-seizure standing posture); d) arterial respiratory alkalosis (pH 7.5 vs. mean reference pH of 7.38) and prolactin elevation (30 µg/L with mean reference level of 15 µg/L), this seizure will be classified as partial complex with emotional, neurologic (loss of awareness for 45 min), hypomotoric (for 65 s), cardiac (43 beat/min increase in rate and ST depression of 2 mm), respiratory (11 breaths/min increase in rate), arterial alkalosis (pH elevated by 0.5) and endocrine (prolactin elevation of 15 ug/L) manifestations. The duration (in sec., min., or hours) of these changes may be included in the quantification/classification for added detail. The spread of this seizure (which was not treated) may be tracked using the temporal evolution of changes in the various indices. The reaction time test failure (28 sec after the first clinical manifestation) and motionlessness are indications that the seizure spread from its emergence network (as amygdala and hippocampus) to other networks such as the contra-lateral hippocampal formation. An unprovoked expression of fear and tachycardia in this patient, may automatically trigger delivery of therapy to either: the commissures (anterior and/or psalterium) connecting the two mesial temporal networks and/or to the unaffected mesial temporal network to prevent invasion by abnormal activity.

The likelihood of spread of abnormal activity, past history of patterns of spread relating to the activity detected, and/or other factors may be utilized to categorize a detected activity for which potential spread activities may be predicted based upon previously known data. In this manner, the activity classification unit 450 classifies the detected activity in order to estimate the conditional probability and extent (spread quotient) of spread and express it quantitatively as between 0-1 or as a percentage (e.g., 60%) or semi-quantitatively (low, medium or high). Moreover, data from the activity mapping unit 410 may be utilized by the activity reference comparison unit 440 to perform a comparison function of the detected activity to previously stored patterns to determine the likelihood of spread.

Turning now to FIG. 5, a simplified, two-dimensional graphical depiction of a mapping of electrical activity in a patient's brain and the probability of spread, in accordance with one embodiment of the present disclosure, is illustrated. Sites 505 and 510 have similar or coupled activity, as do sites 515 and 520, and 525 and 530. Sites 535 and 540 have dissimilar or uncoupled activity, as do sites 545 and 550. Gradients 555-575 represent the degree of anatomical and/or functional connectivity between sites 505-510, 515-520, 525-530, 545-540, and 545-550, respectively. The thickness of the arrows depicting gradients 555-575 corresponds to the relative magnitude of the anatomical and/or functional connectivity between the connected sites; functional connectivity may rapidly change as a function of level of consciousness, local metabolic-ionic conditions etc., and anatomical connectivity may also change (albeit at much slower rate than functional connectivity) due, for example, to injury to brain tissue, among other causes.

From this, the following assessments of the spread of abnormal activity between two sites can be made: Spread from 505 to 510 via gradient 555: highly likely (coupled/similar activity combined with a high-magnitude gradient). Spread from 515 to 520 via gradient 560: unlikely (coupled activity is associated with the lowest-magnitude gradient in this figure). Spread from 525 to 530 via gradient 565: likely (coupled activity combined with a medium-magnitude gradient). Spread from 535 to 540 via gradient 570: unlikely (uncoupled activity is associated with a medium-magnitude gradient). Spread from 545 to 550 via gradient 575: likely (uncoupled activity is associated with the highest-magnitude gradient in this figure). Gradient magnitude may affect coupling degree between nodes/networks and vice versa.

The medical device 200 may utilize the electrical activity mapping information depicted in FIG. 5 to selectively treat nodes, hubs, or networks susceptible to invasion by abnormal electrical activity and/or preventively target uninvolved but potentially recruitable/entrainable (over weeks, months or years) nodes, to decrease the development of more epileptogenic networks. Specifically, in one embodiment, this disclosure will reduce or prevent secondary epileptogenesis. Secondary epileptogenesis is the process of transformation by epileptogenic networks, of those connected to them which were not epileptogenic, as exemplified by the so-called "mirror-focus" phenomenon: A naïve hippocampal region contralateral to that which was rendered epileptogenic, will after certain time generate epileptiform discharges synchronously with the epileptogenic network. If the original epileptogenic network is not suppressed or disconnected from the naïve one at this stage, the naïve will in time become also epileptogenic in an autonomous way. The plasticity changes required for epileptogenic transformation of a network by another will be addressed in one embodiment of this disclosure by selective blockage of conduction of abnormal electrical impulses between an epileptogenic and a naïve network; for example, epileptiform discharges in the epileptogenic network will trigger (via a device) a therapy to cause a conduction block in the path(s) connecting the abnormal and naïve network, or trigger impulses in said path(s) in a direction opposite the abnormal ones and in a timely manner to cause them to collide, thus preventing their arrival to the naïve network. The kindling phenomenon is another example of plastic changes triggered by initially sub-liminal activation of neural structure(s) that, over time, manifest as seizures.

The targeting and/or sensing of particular areas of electrical activity and/or potential electrical activity may be made for treatment in a number of ways that would be known to those skilled in the art having benefit of the present disclosure. FIGS. 6A and 6B illustrate one such example. Turning now to FIGS. 6A and 6B, a stylized depiction of a sensor/electrode array mesh 610, in accordance with one embodiment of the present disclosure, is illustrated. FIG. 6A depicts a sensor/electrode array 620 that may be embedded or integrated into the array mesh 610. The sensor/electrode array mesh 610 is depicted as a mesh-type unit for illustrative purposes only and those skilled in the art would be able to implement a variety of types of sensor/electrode arrays and remain within the spirit and scope of the present disclosure. The array mesh 610 may comprise a plurality of sensors and/or electrodes positioned in any number of configurations, such as a row-column array.

FIG. 6B illustrates a top view of the array mesh 610, in accordance with one embodiment of the present disclosure. The array mesh 610 may be formed such that a predetermined arrangement of sensors and electrodes are configured in a manner such that various portions of the brain may be targeted for treatment (e.g., electrical stimulation). The sensors/electrodes array 620 may include positioning the sensors and electrodes such that target specific locations/networks in the brain. Alternatively, the array of sensors/electrodes array 620 may include sensor and electrode elements that are capable of effectuating brain contact from a subcutaneous placement. The arrays may be interconnected electrically via wires 630 that may be coupled to an external device that can provide signals and/or power for controlling the operations of the sensor/electrode array mesh 610. In this manner, the various mapped locations of electrical activity and/or potential electrical activity described in the context of FIG. 4, may be targeted for treatment. Data from the electrical activity zone unit 297 may be sent to a processing unit within a medical device to control the activation of various sensors and/or electrodes in the sensor/electrode array mesh 610, thereby being capable of providing targeted treatment for diminishing electrical activity and/or reducing the possibility of the occurrence of electrical activity in a patient's body. The array 610 may be also populated by chemical, optical, thermal, and/or pressure sensors and therapy elements.

Turning now to FIGS. 7A-7D, a stylized depiction of an electrical activity and its relationship to a potential spread location, in accordance with one embodiment of the present disclosure, is provided. Based upon the data resulting from the comparison performed by the activity reference comparison unit 340, a determination may be made as to the likelihood of the spread, direction and/or intensity of detected abnormal activity. The comparison may be based upon data stored in memory (e.g., memory 217) and/or look-up tables or contemporaneous data.

FIG. 7A illustrates a stylized depiction of an exemplary abnormal activity detected in a site 710 of a patient's brain. Based upon this detection, the activity reference comparison unit 440 (FIG. 4) may perform a look-up comparison, and may identify a stored abnormal activity mapping that is similar to that of the activity occurring at site 710 in FIG. 7A.

FIG. 7B illustrates a stylized depiction of a stored reference spread mapping of activity that includes activity at site 710 and sites 720, 720A where the abnormal activity may spread via gradients 730, 730A, respectively. Gradient 730 is much greater in magnitude than gradient 730A. However, as discussed supra, the degree of coupling of site 710 with sites 720 and 720A and the magnitudes of gradients 730 and 730A may vary depending on time of day, mental task, etc. This reference spread mapping may be stored in memory 217, or alternatively, in the local database unit 255 and/or the database unit 250.

FIG. 7C illustrates a stylized depiction of a "real-time" mapping of one or more of the degree of coupling of site 710 with 720 and/or 720A, the gradients 730 and/or 730A, or any abnormal activity spread. In the depicted embodiment of FIG. 7C, it is found that the "real-time" mapping matches the reference spread mapping shown in FIG. 7B. As a result, it may be concluded that spread from 710 to 720 is highly likely, and an intervention to prevent spread from 710 to 720 may be implemented. It may also be concluded that spread from 710 to 720A is unlikely, and an intervention to prevent spread from 710 to 720A is not required.

FIG. 7D illustrates a stylized depiction of a "real-time" mapping, similar to the depiction shown in FIG. 7C. In the depicted embodiment of FIG. 7D, it is found that the "real-time" mapping fails to match the reference spread mapping shown in FIG. 7B. For example, the patient may be performing a different mental task, may be in a different body state, etc. Particularly, it is found that gradient 730A is much greater in magnitude than gradient 730. As a result, it may be concluded that spread from 710 to 720 is unlikely, and an intervention to prevent spread from 710 to 720 is not required. It may also be concluded that spread from 710 to 720A is highly likely, and an intervention to prevent spread from 710 to 720A may be implemented.

FIG. 8 shows a flowchart depiction of a method, in accordance with one illustrative embodiment of the present disclosure. In the depicted method, an epileptic event in a neural network within a brain of a patient may be detected at 810, wherein the epileptic event emerges in a first node of the neural network. The detection may be made based on the appearance of abnormal electrical activity in at least one region of the patient's brain.

After the detecting at 810, a second node of the neural network susceptible to invasion by abnormal activity may be identified at 820, based at least in part on at least one coupling characteristic between the first node and the second node. The at least one coupling characteristic may be selected from an information measure such as phase synchronization, entropy, coherence, etc., as shown in FIG. 2 and/or discussed supra with relation to FIG. 2. In response to the detecting at 810, a therapy may be applied to the second node or any connection to the second node. Exemplary therapies include those described under the discussion as shown in FIG. 1.

Applying the therapy to the second node or a connection thereto may prevent spread of the epileptic event to the second node. Depending on the nature of the connectivity between the first node and the second node, applying the therapy to the second node may also lead to attenuation or termination of the epileptic event in the first node.

The therapy may be applied at any time during the epileptic event. In a particular embodiment, applying the therapy may be performed prior to the spread of the epileptic event to the second node.

Applying the therapy may be based upon detecting an indication of said epileptic event, about to spread, spreading or having spread to said second node.

In an exemplary embodiment, the therapy may be a single electrical stimulation pulse. Alternatively or in addition, the second node or any connection thereto may be at least one of the patient's brain, a target portion of the patient's brain, a cranial nerve of the patient, or a target portion of the cranial nerve of the patient.

Optionally, the method depicted in FIG. 8 may further comprise determining at 840 at least one seizure spread characteristic indicative of a spread of the epileptic event from the first node, wherein the characteristic comprises at least one of a result of at least one of a cognitive test, an awareness test, a responsiveness test, and a chemical assay administered to said patient; or a change in at least one of an autonomic index, a neurologic index, a metabolic index, an endocrine index, a tissue stress marker index, a physical fitness index, a body integrity index, a quality of life index, or a seizure burden index. More information regarding these tests and indices can be found in U.S. patent application Ser. No. 12/756,065, filed Apr. 7, 2010; U.S. patent application Ser. No. 12/770,562, filed Apr. 29, 2010; U.S. patent application Ser. No. 12/896,525, filed Oct. 1, 2010; U.S. patent application Ser. No. 13/040,996, filed Mar. 4, 2011; U.S. patent application Ser. No. 13/091,033, filed Apr. 20, 2011; and U.S. patent application Ser. No. 13/098,262, filed Apr. 29, 2011; incorporated by reference above.

In one embodiment, identifying at 820 the second node may be based at least in part on the at least one seizure spread characteristic determined at 840. In one embodiment, optionally the method may further comprise identifying at 850 at least one pathway from the first node to the second node, based at least in part on the determining at 840. The method may optionally further comprise applying at 860 a therapy to the pathway identified at 850.

FIG. 9 shows a flowchart depiction of a method, according to one illustrative embodiment of the present disclosure. A first body index indicative of an epileptic activity in a patient may be determined at 910. The first body index may be at least one of an autonomic index, a neurologic index, a metabolic index, an endocrine index, a tissue stress marker index, a physical fitness index, a body integrity index, a quality of life index, or a seizure burden index. In one embodiment, the first body index may be a non-electrocortical neurologic index.

In response to the determining at 910, a second body index different from the first body index may be monitored at 920. Monitoring at 1020 may be initiated based upon a change in the first body index. For example, if the first body index is heart rate, an increase in heart rate may be indicative of an epileptic event and thus render it desirable to monitor a second body index to acquire more information relating to the possibility of spread of the epileptic event.

The second body index may be at least one of an autonomic index (different from the first), a neurologic index, a metabolic index, an endocrine index, a tissue stress marker index, a physical fitness index, a body integrity index, a quality of life index, or a seizure burden index. In one embodiment, the second body index may be a non-neurologic index.

Although the second body index is different from the first body index, the second body index may be derived from the same body signal as the first body index. By way of non-limiting example, the first body index may be heart rate (HR) and the second body index may be heart rate variability (HRV), which are different indices both derivable from one signal of cardiac activity (e.g., EKG, etc).

Based on at least the second body index, an indication of epileptic activity spread in a brain of the patient may be detected at 930. As an example of such a detection, a body index indicative of an abnormal motor activity of the patient may be indicative of a spread of epileptic activity to a region of the brain controlling motor activity.

A responsive action may be taken in response to the detecting at 930. The responsive action may be selected from delivering at 940 a therapy to at least one neural structure of the patient, modifying at 950 a therapy to at least one neural structure of the patient, logging at 960 the indication of spread, or warning at 970 said patient, a caregiver, or a medical professional of the indication of spread.

Turning now to FIG. 10, a flowchart depiction of a method, according to one illustrative embodiment of the present disclosure, is presented. Detecting an epileptic event at 1010 may be performed substantially as described above.

A first therapy may then be applied at 1020 to a first neural structure of the patient for treating said epileptic event. The therapy may be an electrical therapy, a thermal therapy, a chemical therapy, or a mechanical (e.g., pressure) therapy, among others, as described above. The first neural structure may be any neural structure encompassing one or more neural networks. In one embodiment, the first neural structure comprises the first node of the first neural network in which the epileptic event is detected at 1010.

A second therapy may be applied at 1130 to a second neural structure, based on a proclivity of a spread of said epileptic event to a third neural structure of said patient. For example, if the proclivity of spread is deemed sufficiently high, the second therapy may be applied at 1130. The proclivity of spread may be determined roughly contemporaneously with the time of performance of the detecting at 1010 and/or applying the first therapy at 1020, or it may be previously determined through retrospective analysis of epileptic events of the patient and/or the spread database thereof. One or more previously determined proclivity(ies) of spread may be stored in a look up table, such as a look up table in memory 217 of the medical device 200.

The second therapy may be the same as or different from the first therapy, and may be as described above.

The second neural structure (to which the second therapy is applied) and the third neural structure (to which the epileptic event may have a proclivity of spread) may be the same or different neural structures.

Any method depicted in FIGS. 8-10 may be performed by a non-transitive, computer-readable storage device for storing instructions that, when executed by a processor, perform the method.

FIGS. 11-12 depict exemplary mechanisms by which epileptic event spread in an exemplary neural network in the brain of a patient may be prevented, delayed, or reduced. In both figures, the model neural network contains three nodes, A, B, and C, with connections between each pair of nodes shown by lines. The thickness of the line reflects the strength of the connection between nodes (thicker lines representing stronger anatomo-functional connections), and arrows represent the direction of electrical impulse propagation.

Turning to FIG. 11, and starting from the non-epileptic brain network, a pro-epileptogenic influence (e.g., trauma to the head) alters weightings and/or directions of the depicted functional connections, converting it into an epileptogenic network. Node A sends excitatory impulses to nodes B and C, which in turn send back inhibitory or disfacilitatory (not shown for simplicity's sakes) to node A. The plastic changes caused by trauma have weakened nodes B and C, leaving node A disinhibited. In the event of an epileptic event emerging at node A, one or more of three depicted interventions may be performed. In one intervention, node A, may be inhibited or disfacilitated, thus lowering the intensity impulses and their rate of propagation toward B and C. In another intervention, signals traveling from A to B or C may be shunted out of the network or fragmented. In another intervention, nodes B and/or C may be excited facilitated or disinhibited, thus restoring their inhibitory feedback to node A. Conduction block (electrical, thermal, chemical or mechanical) of the paths connecting node A to B and C may be undertaken to interfere with the arrival of excitatory impulses to these 2 nodes or the flow of inhibitory input from them to A may be increased.

FIG. 12 shows a non-epileptogenic network that was transformed into epileptogenic through plastic changes through weakening (not shown in the figure) of inhibitory activity flowing from this node to nodes B and C. The disinhibition of nodes B and C results in a marked increase and apparent reversal of flow of information into A. Seizure spread may be prevented by exciting node A, disfacilitating or inhibiting nodes B and C or impeding/shunting/fragmenting the flow of impulses through the paths that connect them.

FIGS. 11 and 12 should be viewed as simplified (even oversimplified) depictions of brain networks, as they lack details about connections (e.g., reciprocal, collateral, etc) and their topology/structure at certain scales. In isolation, the depicted networks may or may not support seizure emergence. In the brain, the depicted networks may be influenced by other networks in a manner that supports seizure emergence in the depicted (simplified) networks.

FIGS. 13-25 review various neural networks known in the brain. In these figures, the weight of the line reflects the strength of the functional connectivity between nodes (thicker lines representing more active connections), and arrows represent the direction of action potential propagation. These figures represent various neural networks to which the teachings of this disclosure may be applied.

Turning to FIG. 13, the following brain regions are depicted: rFIC, right hemisphere frontoinsular cortex, containing the ventrolateral prefrontal cortex and anterior insula; PCC, posterior cingulate cortex; rPPC, right hemisphere posterior parietal cortex; rDLPFC, right hemisphere dorsolateral prefrontal cortex; VMPFC, ventromedial prefrontal cortex; and ACC, anterior cingulate cortex. These brain regions are members of three networks, shown by cross-hatching: central executive network (diagonal lines), default mode network (stipples), and salience network (vertical lines).

Figure 13C:
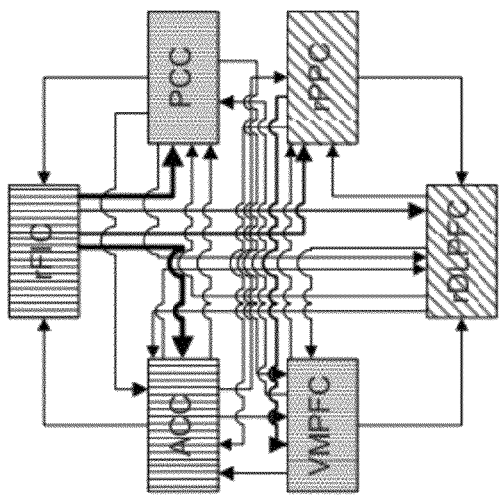
Figure 13B:
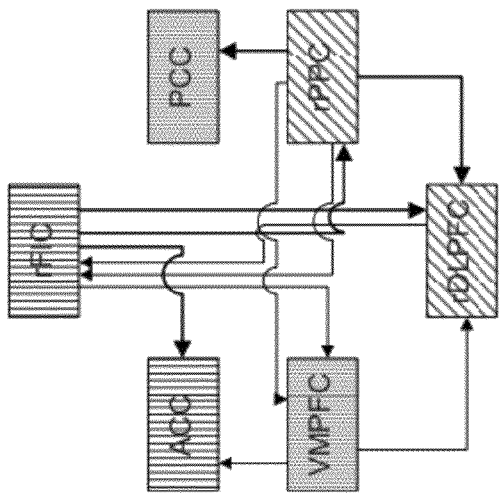
Figure 13A:
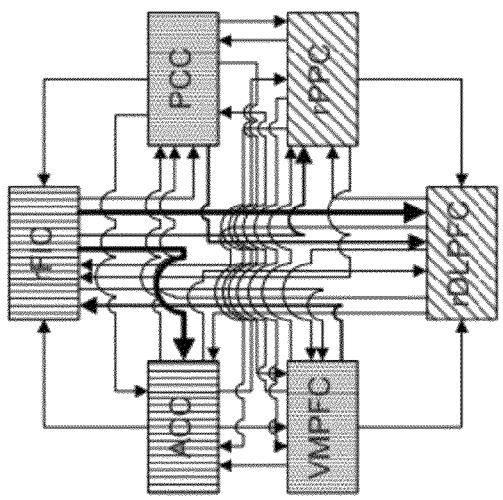

FIG. 13 shows functional connectivity under three different conditions. FIG. 13A shows typical functional connectivity when the subject performs an auditory event segmentation task (e.g., listening to two different sound sources). FIG. 13B shows typical functional connectivity when the subject performs a visual "oddball" attention task. FIG. 13C shows typical functional connectivity when the subject is in a task-free state.

Turning to FIG. 14, various brain regions are shown. Four particular pathways between nodes are shown: 1, mammillothalamic tract; 2, fornix; 3, stria terminalis; 4, ansa peduncularis. Together, the depicted brain regions and the pathways between them may be considered a neural network.

Turning to FIG. 15, various brain regions are shown. Each of the depicted pathways is a monosynaptic reciprocal connection, and arrowheads are omitted. Together, the depicted brain regions and the pathways between them may be considered a neural network.

Turning to FIG. 16, various brain regions are shown, with afferences (signals from the body to the brain) also depicted. Five particular pathways between nodes are shown: 1, post-commissural fornix; 2, mammillo-thalamic tract; 3, cingulate gyrus; 4, pre-commissural fornix; 5, medial forebrain bundle. Together, the depicted brain regions and the pathways between them may be considered a neural network.

Turning to FIG. 17, various brain regions are shown. Together, the depicted brain regions and the pathways between them may be considered a neural network.

Turning to FIG. 18, various brain regions are shown. Together, the depicted brain regions and the pathways between them may be considered a neural network. The stippled structures and the pathways between them may together be considered a subnetwork.

Turning to FIG. 19, various brain regions are shown. The depicted bidirectional connections generally comprise afferent projections to, and efferent projections from, the amygdaloid complex. Together, the depicted brain regions and the pathways between them may be considered a neural network. The amygdaloid complex may be considered the hub of the depicted neural network.

Turning to FIG. 20, various brain regions are shown. The depicted bidirectional connections generally comprise afferent projections to, and efferent projections from, the septal region. Together, the depicted brain regions and the pathways between them may be considered a neural network. The septal region may be considered the hub of the depicted neural network.

Turning to FIG. 21, various brain regions are shown. The depicted bidirectional connections generally comprise afferent projections to, and efferent projections from, the amygdaloid complex. The unidirectional connections include the following: afferent projections from the mammillary bodies to the anterior thalamic nucleus, from the anterior thalamic nucleus to the presubiculum, from the subiculum to the hippocampus, from the parasubiculum to the hippocampus, and from the temporal neocortex to the cingulate gyrus; and efferent projections from the cingulate gyrus to each of the subiculum, parasubiculum, presubiculum, hippocampus, the superior colliculi, pretectal area, periaqueductal gray matter, midbrain tegmentum, nucleus locus coeruleus, pontine gray, and dorsomedial thalamaic nucleus, from the mammillary bodies to the pontine gray and the nucleus reticularis tegmentis pontis. Together, the depicted brain regions and the pathways between them may be considered a neural network. The cingulate gyms may be considered the hub of the depicted neural network.

Turning to FIG. 22, the Papez circuit is depicted. Together, the depicted brain regions and the pathways between them may be considered a neural network.

Turning to FIG. 23, various brain regions are shown. All unidirectional connections are afferent connections, except for the connection from the habenula to the mesencephalic reticular formation, which is efferent. Together, the depicted brain regions and the pathways between them may be considered a neural network.

Turning to FIG. 24, various brain regions are shown. The unidirectional connections include the following: afferent projections from the Raphe nucleus, nucleus locus coeruleus, and medial entorhinal area to the hippocampus and subiculum; from the olfactory bulb, prepiriform cortex, periamygdaloid cortex, septum, (dorsal) Raphe nucleus, and nucleus locus coeruleus to the lateral entorhinal area; and from the (dorsal) Raphe nucleus, nucleus locus coeruleus, thalamus, and septum to the medial entorhinal area; and efferent projections from the hippocampus and subiculum to the cingulate gyms, anterior commissure, mammillary bodies, anterior thalamic nucleus, periaqueductal gray, and pontine nucleus; and from CA3 and the presubiculum to the medial entorhinal area. Together, the depicted brain regions and the pathways between them may be considered a neural network. The hippocampus and subiculum, and the entorhinal area, may be considered as two hubs of the depicted neural network.

Turning to FIG. 25, various brain regions are shown. Together, the depicted brain regions and the pathways between them may be considered a neural network.

All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims. It should be especially apparent that the principles of the disclosure may be applied to selected cranial nerves other than, or in addition to, the vagus nerve to achieve particular results in treating patients having epilepsy, depression, or other medical conditions.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below.

What is claimed is:

1. A non-transitive, computer-readable storage device for storing data that when executed by a processor, perform a method, comprising:
   determining a first body index indicative of an epileptic activity in a patient;
   monitoring a second body index different from the first body index, in response to said determining;
   detecting an indication of epileptic activity spread in a brain of the patient, based upon at least said second body index, comprising determining a spread quotient relating to said epileptic event, said spread quotient comprising information relating to at least one or more of a probability of a spread of said epileptic activity, a speed of said spread of said epileptic activity, a location of said epileptic activity, or a direction of said spread of said epileptic event; and
   taking a responsive action in response to said detecting, wherein said responsive action is selected from delivering a therapy to at least one neural structure of said patient, modifying a therapy to at least one neural structure of said patient, logging said indication of spread, or warning said patient, a caregiver, or a medical professional of said indication of spread.

2. The non-transitive, computer-readable storage device of claim 1, wherein said first body index is a non-electrocortical neurologic index, and said second body index is a non-neurologic index.

3. The non-transitive, computer-readable storage device of claim 1, wherein said second body index is derived from the same body signal as the first body index.

4. The non-transitive, computer-readable storage device of claim 1, wherein said first body index is selected from an autonomic index, a neurologic index, a metabolic index, an endocrine index, a tissue stress marker index, a physical fitness index, a body integrity index, a quality of life index, or a seizure burden index, and said second body index is selected from an autonomic index, a neurologic index, a metabolic index, an endocrine index, a tissue stress marker index, a physical fitness index, a body integrity index, a quality of life index, or a seizure burden index.

5. The non-transitory computer readable program storage unit of claim 1, wherein said first body index is a cardiac index and said second body index is a motor activity index.

6. The non-transitive, computer-readable storage device of claim 5, wherein the cardiac index is selected from heart rate (HR), HR variability (HRV), or electrocardiogram (EKG) complex morphology, and the motor activity index is selected from an amplitude of a body movement, a direction of the body movement, or a force of the body movement.

7. The non-transitory computer readable program storage unit of claim 1, wherein said first body index is HR and said second body index is HRV.

8. The non-transitory computer readable program storage unit of claim 1, wherein said therapy comprises at least one of an electrical therapy, a thermal therapy, a chemical therapy, a cognitive therapy, or a mechanical therapy.

9. The non-transitory computer readable program storage unit of claim 8, wherein said therapy is an electrical therapy applied to a cranial nerve, a region or node of a spinal cord, or a peripheral nerve.

\* \* \* \* \*